(12) United States Patent
Niwa et al.

(10) Patent No.: US 8,165,265 B2
(45) Date of Patent: Apr. 24, 2012

(54) METHOD OF CONSTRUCTING MULTI-TOMOGRAPHIC IMAGE AND DIGITAL 3 D X-RAY PHOTOGRAPHING APPARATUS

(75) Inventors: Katsumi Niwa, Tochigi (JP); Takanori Wagatsuma, Tokyo (JP); Hisanori Nakahama, Tokyo (JP)

(73) Assignee: Yoshida Creation Inc., Tokyo (JP)

( * ) Notice: Subject to any disclaimer, the term of this patent is extended or adjusted under 35 U.S.C. 154(b) by 0 days.

(21) Appl. No.: 12/002,820

(22) Filed: Dec. 19, 2007

(65) Prior Publication Data

US 2008/0273653 A1 Nov. 6, 2008

(30) Foreign Application Priority Data

Dec. 27, 2006 (JP) ................................ 2006-353528

(51) Int. Cl.
*A61B 6/14* (2006.01)
*H05G 1/60* (2006.01)
*G01N 23/04* (2006.01)
(52) U.S. Cl. .............. 378/39; 378/4; 378/27; 378/98.12
(58) Field of Classification Search ................ 378/4, 21, 378/38–40, 27, 98.12
See application file for complete search history.

(56) References Cited

U.S. PATENT DOCUMENTS

| | | | | |
|---|---|---|---|---|
| 5,195,114 | A * | 3/1993 | Sairenji et al. | 378/40 |
| 5,784,429 | A * | 7/1998 | Arai | 378/38 |
| 6,049,584 | A * | 4/2000 | Pfeiffer | 378/39 |
| 6,289,074 | B1 * | 9/2001 | Arai et al. | 378/4 |
| 6,570,953 | B1 * | 5/2003 | Dobert et al. | 378/21 |
| 7,039,156 | B2 * | 5/2006 | Arai et al. | 378/39 |
| 7,336,763 | B2 * | 2/2008 | Spartiotis et al. | 378/40 |
| 7,397,890 | B2 * | 7/2008 | Sukovic et al. | 378/38 |
| 2008/0226150 | A1 * | 9/2008 | Sadakane | 382/131 |
| 2008/0232539 | A1 * | 9/2008 | Pasini et al. | 378/4 |

FOREIGN PATENT DOCUMENTS

JP 2004-180944 7/2006

* cited by examiner

*Primary Examiner* — Edward Glick
*Assistant Examiner* — Thomas R Artman
(74) *Attorney, Agent, or Firm* — Jordan and Hamburg LLP

(57) ABSTRACT

Tomographic images in a plurality of radius places are obtained in one-time X-ray photographing, and a lot of information on the diagnose can be provided by forming a stereoscopic image with these obtained tomographic images, and thickness of radial and fineness of angular direction of tomographic image that can be obtained herein compared with prior art can be set arbitrary and can be adjusted thereby obtaining further imperceptible stereoscopic image. To this end, whole photographed images at respective divided unit angles that can be obtained in the digital dental panoramic radiography apparatus at the tomography in the circular orbit, are stored, after X-ray photographed, these photographed images are arranged substantially on the circular arc at the radius place of the tomographic image of the desired extracting part, tomographic images in radius location can be constructed by adding while shifting every photograph unit angle.

6 Claims, 53 Drawing Sheets

| | | | | | | | | | |
|---|---|---|---|---|---|---|---|---|---|
| | | | | | | | | | XXI<br>M/2+N/2<br>k |
| | | | | | | | | XX<br>M<br>j x 1/3+<br>k x 2/3 | XX<br>L/2+M/2<br>j |
| | | | | | | | XIX<br>L/2+M/2<br>j x 2/3+<br>k x 1/3 | XIX<br>L<br>i x 1/3+<br>j x 2/3 | XIX<br>K/2+L/2<br>i |
| | | | | | | XVIII<br>L<br>j | XVIII<br>K/2+L/2<br>i x 2/3+<br>j x 1/3 | XVIII<br>K<br>h x 1/3+<br>i x 2/3 | XVIII<br>J/2+K/2<br>h |
| | | | | | XVII<br>K/2+L/2<br>i x 1/3+<br>j x 2/3 | XVII<br>K<br>i | XVII<br>J/2+K/2<br>h x 2/3+<br>i x 1/3 | XVII<br>J<br>g x 1/3+<br>h x 2/3 | XVII<br>I/2+J/2<br>g |
| | | | | XVI<br>J/2+K/2<br>h x 1/3+<br>i x 2/3 | XVI<br>J<br>h | XVI<br>I/2+J/2<br>g x 2/3+<br>h x 1/3 | XVI<br>I<br>f x 1/3+<br>g x 2/3 | | XVI<br>H/2+I/2<br>f |
| | | | XV<br>I/2+J/2<br>g x 1/3+<br>h x 2/3 | XV<br>I<br>g | XV<br>H/2+I/2<br>f x 2/3+<br>g x 1/3 | XV<br>H<br>e x 1/3+<br>f x 2/3 | | | |
| | | XIV<br>H/2+I/2<br>f x 1/3+<br>g x 2/3 | XIV<br>H<br>f | XIV<br>G/2+H/2<br>e x 2/3+<br>f x 1/3 | | | | | |
| | XIII<br>G/2+H/2<br>e x 1/3+<br>f x 2/3 | XIII<br>G<br>e | | | | | | | |
| XII<br>F/2+G/2<br>d x 1/3+<br>e x 2/3 | | | | | | | | | |
| Frame 12 | Frame 13 | Frame 14 | | Frame 15 | | Frame 16 | | | |

FIG.7C

| | | | | | | | | | | XII<br>I<br>h |
|---|---|---|---|---|---|---|---|---|---|---|
| | | | | | | | | X<br>H<br>g x 2/3+<br>h x 1/3 | XI<br>H<br>g | |
| | | | | | | VIII<br>G<br>f x 1/3+<br>g x 2/3 | IX<br>G<br>f x 2/3+<br>g x 1/3 | X<br>G<br>f | | |
| | | | | VI<br>F<br>f | VII<br>F<br>e x 1/3+<br>f x 2/3 | VIII<br>F<br>e x 2/3+<br>f x 1/3 | IX<br>F<br>e | | | |
| | | | V<br>E<br>e | VI<br>E<br>d x 1/3+<br>e x 2/3 | VII<br>E<br>d x 2/3+<br>e x 1/3 | VIII<br>E<br>d | | | | |
| | | IV<br>D<br>d | V<br>D<br>c x 1/3+<br>d x 2/3 | VI<br>D<br>c x 2/3+<br>d x 1/3 | VII<br>D<br>c | | | | | |
| | III<br>C<br>c | IV<br>C<br>b x 1/3+<br>c x 2/3 | V<br>C<br>b x 2/3+<br>c x 1/3 | | | | | | | |
| II<br>B<br>b | III<br>B<br>a x 1/3+<br>b x 2/3 | | | | | | | | | |
| I<br>A<br>a | | | | | | | | | | |

← X axis direction

Frame 1   Frame 3   Frame 5   Frame 7

FIG. 10A

| | | | | | | | |
|---|---|---|---|---|---|---|---|
| | | | | | | | XX<br>M<br>j x 1/3+<br>k x 2/3 |
| | | | | | XVIII<br>L<br>j | XIX<br>L<br>i x 1/3+<br>j x 2/3 |
| | | | XVI<br>K<br>i x 2/3+<br>j x 1/3 | XVII<br>K<br>i | XVIII<br>K<br>h x 1/3+<br>i x 2/3 |
| | | XIV<br>J<br>h x 1/3+<br>i x 2/3 | XV<br>J<br>h x 2/3+<br>i x 1/3 | XVI<br>J<br>h | XVII<br>J<br>g x 1/3+<br>h x 2/3 |
| | XIII<br>I<br>g x 1/3+<br>h x 2/3 | XIV<br>I<br>g x 2/3+<br>h x 1/3 | XV<br>I<br>g | XVI<br>I<br>f x 1/3+<br>g x 2/3 | |
| | XII<br>H<br>f x 1/3+<br>g x 2/3 | XIII<br>H<br>f x 2/3+<br>g x 1/3 | XIV<br>H<br>f | XV<br>H<br>e x 1/3+<br>f x 2/3 | |
| XI<br>G<br>e x 1/3+<br>f x 2/3 | XII<br>G<br>e x 2/3+<br>f x 1/3 | XIII<br>G<br>e | | | |
| X<br>F<br>d x 1/3+<br>e x 2/3 | XI<br>F<br>d x 2/3+<br>e x 1/3 | | | | |
| IX<br>E<br>c x 1/3+<br>d x 2/3 | | | | | |

Frame 9    Frame 11    Frame 13    Frame 15

X axis direction →

Frame 1

| I<br>A<br>a | II<br>B<br>b | III<br>C<br>c | IV<br>D<br>d | V<br>E<br>e | VI<br>F<br>f |

Frame 4

| IV<br>B/2+C/2<br>b | V<br>C/2+D/2<br>c | VI<br>D/2+E/2<br>d | VII<br>E/2+F/2<br>e | VIII<br>F/2+G/2<br>f | IX<br>G/2+H/2<br>g |

FIG. 13

X axis direction →

| Frame | | | | | | | | | | | |
|---|---|---|---|---|---|---|---|---|---|---|---|
| Frame 1 | I A a | II B b | III C c | IV D d | V E e | VI F f | | | | | |
| Frame 4 | | IV B/2+C/2 b | V C/2+D/2 c | VI D/2+E/2 d | VII E/2+F/2 e | VIII F/2+G/2 f | IX G/2+H/2 g | | | | |
| Frame 7 | | | VII D c | VIII E d | IX F e | X G f | XI H g | XII I h | | | |
| Frame 10 | | | | X E/2+F/2 d | XI F/2+G/2 e | XII G/2+H/2 f | XIII H/2+I/2 g | XIV I/2+J/2 h | XV J/2+K/2 i | | |
| Frame 13 | | | | | XIII G e | XIV H f | XV I g | XVI J h | XVII K i | XVIII L j | |
| Frame 16 | | | | | | XVI H/2+I/2 f | XVII I/2+J/2 g | XVIII J/2+K/2 h | XIX K/2+L/2 i | XX L/2+M/2 j | XXI M/2+N/2 k |

⋮

Obtained tomographic image

| I A a | 2b | 3c | 4d | 5e | 6f |
|---|---|---|---|---|---|

⋰

| 6g | 6h | 6i | 6j | 6k | 6l |
|---|---|---|---|---|---|

⋮

METHOD OF CONSTRUCTING MULTI-TOMOGRAPHIC IMAGE AND DIGITAL 3 D X-RAY PHOTOGRAPHING APPARATUS

BACKGROUND OF THE INVENTION

1. Field of the Invention

The present invention relates to a method of constructing multi tomographic image, in which by storing frame images having whole subject images on the radius of gyration in the large-capacity frame image storage means with panoramic X-ray photographing of one time, and by performing the overlapping process of the frame images, the plural pieces of the frame images forming the tomography on the arbitrary radius of gyration are used to construct a tomographic image of the respective radii of gyration, on the arbitrary radius of gyration easily.

Moreover, the present invention relates to a digital 3 D X-ray photographing apparatus, in which a stereoscopic image can be formed by making the transversal slice images from the tomographic images of respective radii, and by using a volume rendering software.

2. Description of Related Art

As such kind of method of constructing multi-tomographic image and digital 3 D X-ray photographing apparatus, present applicant previously filed "Method of constructing multi-tomographic image and digital 3 D X-ray photographing apparatus" to Japan (refer to Japanese Patent Application No. 375011/2004).

In the method of constructing multi-tomographic image and a digital panoramic radiography apparatus of this prior application, as shown in the FIGS. 1 and 2, all X-ray photographed images at respective angles obtained at tomogram-photographing on the circular orbit are stored, after X-ray photographed, these X-ray photographed images are arranged on a circular arc at the radius place that becomes a reference, the tomographic images at a plurality of radius places are constructed, by adding while moving every shifting amount decided every tomographic image at each radius place. As for the tomographic image that can be obtained by the technique, the thickness of radial is limited to 0.5 mm, therefore, even if the fineness of the angular direction of the array of the circular arc (divided number) is increased, a great degree of mixings of pixel value in the periphery sections are generated ("δ" in FIG. 2), so that expressive power becomes weakened, accordingly, the number of partitions of the angular direction is also limited.

SUMMARY OF THE INVENTION

The present invention has been made on the bases of the above situation, and has for its object to provide a method of constructing multi-tomographic image and a digital 3 D X-ray photographing apparatus, wherein in the digital dental panoramic photographing apparatus, all the frame photographed images at the each division unit angle that can be obtained at the tomogram-photographing on the circular orbit are stored, after X-ray photographed, these photographed images are arranged substantially on a circular arc at the radius place of the tomographic image of the desired extracting part, and then the tomographic image at the arbitrary radius place is constructed by adding while moving every photograph unit angle.

In order to resolve the above problem, according to one aspect of the present invention, there is provided a method of constructing multi tomographic image comprising:

an X-ray source for irradiating X rays onto a subject, an X-ray imaging means for detecting X rays to pass through the subject, a swivel drive means for making an imaging system constituted by oppositely arranging and fixing the X-ray imaging means and the X-ray source at a certain distance, centered on the subject, a frame image storage means for storing image information being obtained by the X-ray imaging means as a frame image, therein, an image processing means for extracting the frame image from the frame image storage means, and for forming a panoramic image with digital processing, a large-capacity processed image storage means for storing the processed image, a whole image display and storing means for displaying and storing each tomographic image in the large-capacity processed image storage means, and an output means for outputting whole image of the whole image display and storing means, whereby in order to construct a multi-tomographic image, the frame image storing means is made to be a large-capacity frame image storage means, a certain frame image taken out of frame images stored in the large-capacity frame image storage means is projected to the value of each pixel at the radius place in the desire location along the X-ray transmission route at photographing as a square cell element of a near-circular arc displayed by polar coordinates, such a process is performed sequentially with respect to each X-ray photographed image, by using the angle rotated while obtaining each X-ray photographed image as a unit angle, the above processed respective X-ray photographed images are added sequentially by shifting every unit angle, and finally, a tomographic image is constructed at the radius place in the desire location.

Moreover, according to the present multi-tomographic image constructing method, transversal slice images are made from the tomographic image of each radius obtained by the method of constructing multi-tomographic image, and the 3D image is generated from the transversal slice images by using a volume rendering software.

In addition, according to another aspect of the present invention, there is provided, a digital 3 D X-ray photographing apparatus comprising:

an X-ray source for irradiating X rays onto a subject, an X-ray imaging means for detecting X rays passing through the subject, a swivel drive means for making an imaging system constituted by oppositely arranging and fixing the X-ray imaging means and the X-ray source at a certain distance, centered on the subject, a large-capacity frame image storage means for storing image information being obtained by the X-ray imaging means as a frame image, therein, an image processing means for extracting the frame image from the large-capacity frame image storage means, and for forming a panoramic image with digital processing, a large-capacity processed image storage means for storing the processed image, a whole image display and storing means for displaying and storing each tomographic image in the large-capacity processed image storage means, and an output means for outputting whole image of the whole image display and storing means, characterized by comprising:

means for storing frame images of plural pieces which have all subject information on radius of gyration, in the large-capacity frame image storage means, by X-ray photographing an imaging system that consists of the X-ray source and X-ray imaging means in one-time operation, means for projecting and arranging a certain frame image taken out of frame images stored in the large-capacity frame image storage means onto the value of each pixel at the radius place in the desire location along the X-ray transmission route at photographing as a square cell element of a near-circular arc displayed by polar coordinates, means for adding sequentially the above processed respective X-ray photographed images, by performing such a process sequentially with respect to each X-ray photographed image, by using the angle rotated while obtaining each X-ray photographed image as a unit angle, and by shifting every unit angle, and finally, a tomographic image being constructed at the radius place in the desire location.

Moreover, according to the present digital 3 D X-ray photographing apparatus, transversal slice images are made from the tomographic image of each radius obtained by the digital 3 D X-ray photographing apparatus, a 3D image is generated by using a volume rendering software, thereby obtaining a stereoscopic image of all diagnosis regions.

According to the present invention, the tomographic images in a plurality of radius places are obtained in one X-ray photographing, and a lot of information on the diagnosis can be provided by forming a stereoscopic image with these obtained tomographic images. Compared with the prior art, the thickness of radial direction and the fineness of the angular direction of the tomography obtained by the present invention can arbitrarily be set and adjusted resulting in a possibility of an imperceptible display further more.

That is, in the digital 3 D X-ray photographing apparatus of the prior application, only the image at intervals of 0.5 mm could be obtained, but, according to the present invention, even at 0.3 mm interval and 0.1 mm interval, the image of further arbitrary place (for example, 0.1 mm interval et al.) from the interval of the prior application can be constructed.

1. Photographing Principle:

The conventional digital dental panoramic photographing apparatus is to use a principle that photographs a single tomographic image. The photographing principle is explained by the dental panoramic tomography apparatus according to the present applicant. Next, a digital 3 D X-ray photographing apparatus of the present invention is explained. As shown in FIG. 3, a pair of an X-ray source 2 for irradiating X rays onto a subject 1, and an X-ray imaging means 3 for detecting X rays passing through the subject 1 are arranged linearly. The subject 1 is positioned at the rotation center of the pair of the X-ray source 2 and the X-ray imaging means 3, and is oppositely secured to the X-ray source 2 and the X-ray imaging means 3 with the constant distance mutually, the X-ray source 2 and the X-ray imaging means 3 shall be swiveled around the subject 1 relatively by a swivel drive means 4, the swivel drive means 4 is used as a rotation axis a, and the X-ray photographing is performed while rotating the rotation axis as the rotation center a, by one rotation. At this time, the subject 1 shall be positioned just under the swivel drive means 4, that is, at the rotation center a. (Refer to Japanese Patent Application opened No. 211200, A/1998)

Then, the CCD sensor being the X-ray imaging means 3, converts the X radiograph transmitted through the subject 1 into a digital electrical signal as a frame image with a constant area, by an A/D conversion means 5. Moreover, a large-capacity frame image storage means 6 for storing image information being obtained by the X-ray imaging means 3 as a frame image, is provided, also, an image processing means 7 for performing an extraction of the frame image and a formation of the arbitrary tomographic plane by digital-processing the panoramic image, a large-capacity processed image storage means 8 for storing the processed image, a whole image display and storing means 9 for displaying respective tomography by the large-capacity processed image storage means 8 are provided, and also an output means 10 for outputting information of the whole image display and storing means 9 (for example an image display device such as CRT displays and liquid crystal panels and a printer for printing out the image), is provided.

Herein, an important thing is that, the above single tomography digital panorama radiography apparatus according to present applicant and the present application use identical panoramic photographing method, and the single tomographic digital panorama radiography apparatus according to the above present applicant uses the CCD sensor, but the present invention uses the TDI (Time Delay Integration) method for the processed signal, so that such a processed signal can not be stored as a frame image.

(Refer to Japanese Patent Application opened No. 211200, A/1998)

BRIEF DESCRIPTION OF THE DRAWINGS

FIG. 6 is an enlarged detail of FIG. 5 showing whole frame images projected in the method of constructing multi-tomographic image according to the present invention;

FIGS. 7A-7D collectively show an explanatory view showing the tomographic image on 300 mm in radius extracted by the method of constructing multi-tomographic image of the prior application to the present invention;

FIGS. 10A-10C collectively show an explanatory view showing the tomographic image on 150 mm in radius extracted by the method of constructing multi-tomographic image of the prior application to the present invention;

FIG. 12 is an enlarged detail of FIG. 11 showing frame images every two frame projected by the method of constructing multi-tomographic image of the prior application to the present invention;

FIG. 13 is an explanatory view showing the tomographic image on 100 mm in radius extracted by the method of constructing multi-tomographic image of the prior application to the present invention;

DETAILED DESCRIPTION OF THE INVENTION

Figure 1:
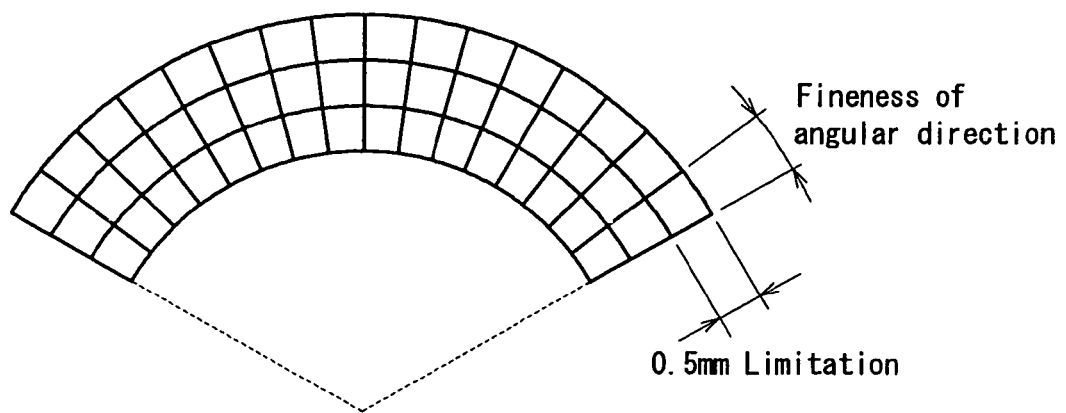
FIG. 1 is an explanatory view showing a circular arc fineness by which the photographed image is arranged in the conventional method of constructing multi-tomographic image.
Figure 2:
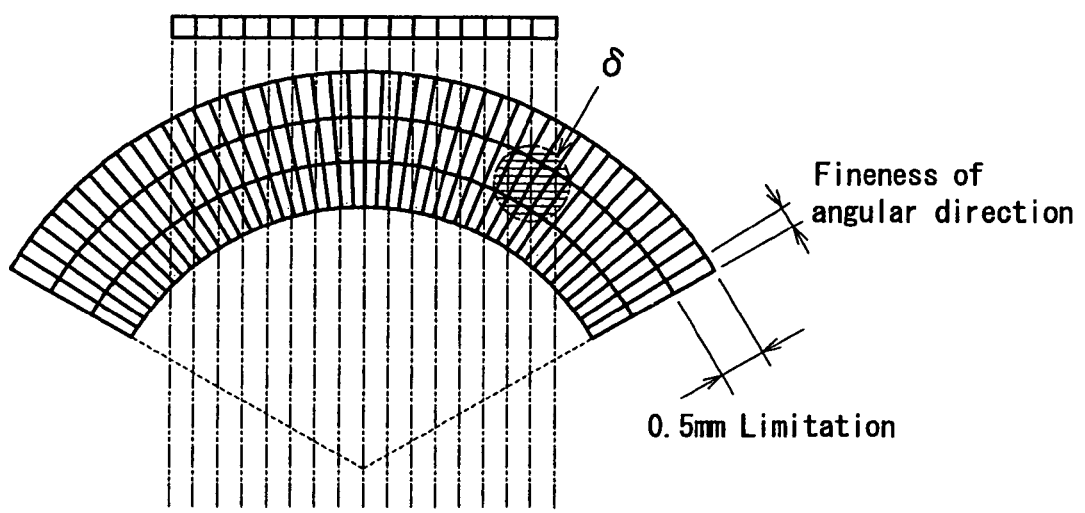
FIG. 2 is an explanatory view showing the limitation of the fineness of the angular direction in the array of the circular arc in the conventional method of constructing multi-tomographic image.
Figure 3:
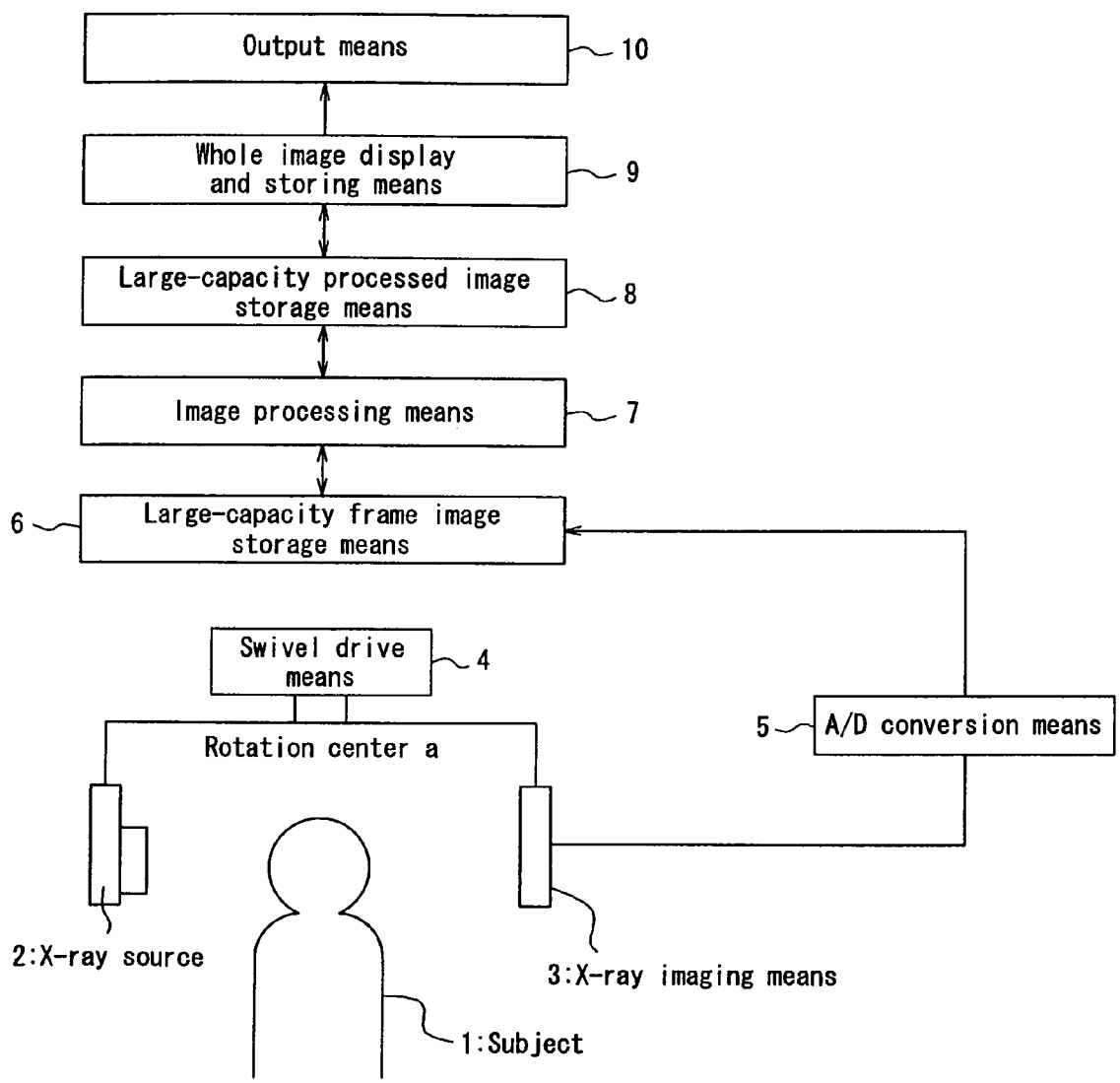
FIG. 3 is a flow chart showing a processing procedure of the method of constructing multi tomography according to the present invention.

Hereinafter, preferred embodiments of the present invention will be described in detail with reference to the drawings.
First Embodiment
Tomography Constructing Method by Frame Interlace Method First, as shown in FIG. 3, a subject 1 is introduced at the position of rotation center of an X-ray source 2 and an X-ray imaging means 3. These X-ray source 2 and X-ray imaging means 3 are arranged oppositely in the direction of the diameter of the circle, are secured to a swivel drive means 4, rotatably, and are arranged in such a manner that the subject 1 is positioned at the rotation center a of these X-ray source 2 and X-ray imaging means 3. The X-ray photographing is performed according to the procedure that X rays are irradiated from the X-ray source 2 while rotating the driving swivel drive means 4, X rays transmitted through the subject 1 are received by the X-ray imaging means 3 (CCD sensor), X-ray images thus obtained are A/D converted by an A/D conversion means 5, and are converted into a digital electrical signal of the frame image, and frame images thus A/D converted are stored in a large-capacity frame image storage means 6.

In this embodiment, it is assumed that X rays irradiated from the X-ray source are parallel beams, and following descriptions are performed.

For example, the pixel size of the CCD sensor is made one line sensor of one vertical pixel×six transversal pixels. and one pixel size of the CCD sensor is made as 100 micrometer, and when X-ray photographing part of the subject positioned on radius gyration of 300 mm is photographed stepwise and continuously while shifting the photographing part by one pixel in the X-ray photographing angle of 360 degrees, the sheet count of frame image stored in the large-capacity frame image storage means 6 is as follows.

Figure 4:
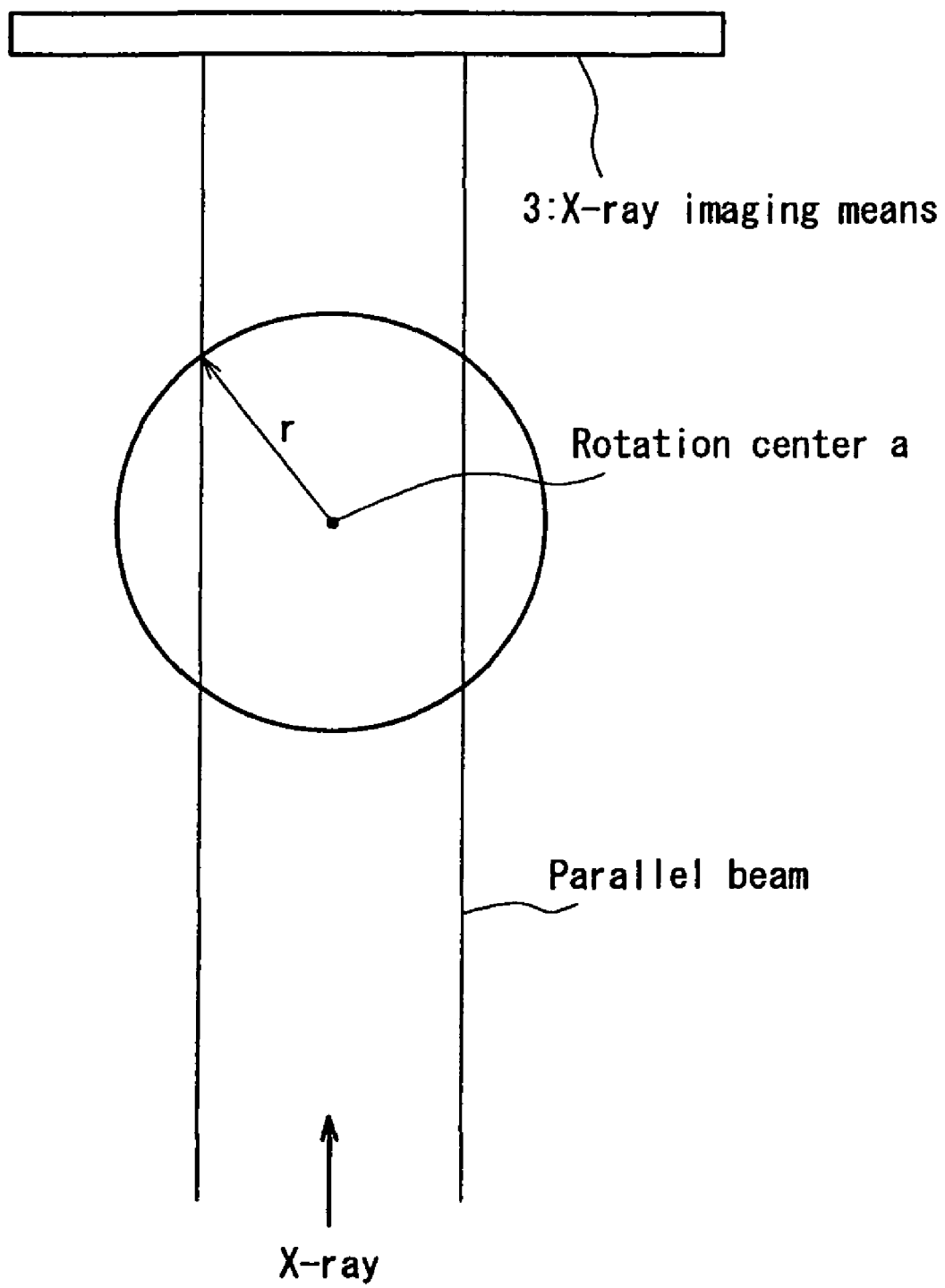
FIG. 4 is an explanatory view showing the state of the radiography of the method of constructing multi tomography according to the present invention.

That is, as shown in FIG. 4, the X-ray source 2 (not shown in FIG. 4) and the X-ray imaging means 3, that receives the parallel beam irradiated from the X-ray source 2, are rotated usually centered on the rotation center a by the swivel drive means 4 (not shown), when the x-ray radiography of one revolution is performed, the tomography on radius r from the rotation center a, can be obtained.

In this case, (a) The circumference of radius 300 mm becomes $2\pi r=1884$ mm. Here, the obtained frame sheet count is assumed to be n. when the X-ray photographing is performed by shifting by one pixel, the pixel size of one pixel of the CCD sensor is made 100 micrometer, so that the sheet count n of the frame obtained on the radius 300 mm, become n=1884000 micrometer/100 micrometer=18840 piece.

That is, 18840 frame images are stored in the large-capacity frame image storage means 6. Then, the frame images stored in the large-capacity frame image storage means 6 is used to construct an arbitrary tomographic image with the use of "Frame-interlace method" that explains hereinafter.

Figure 5A:
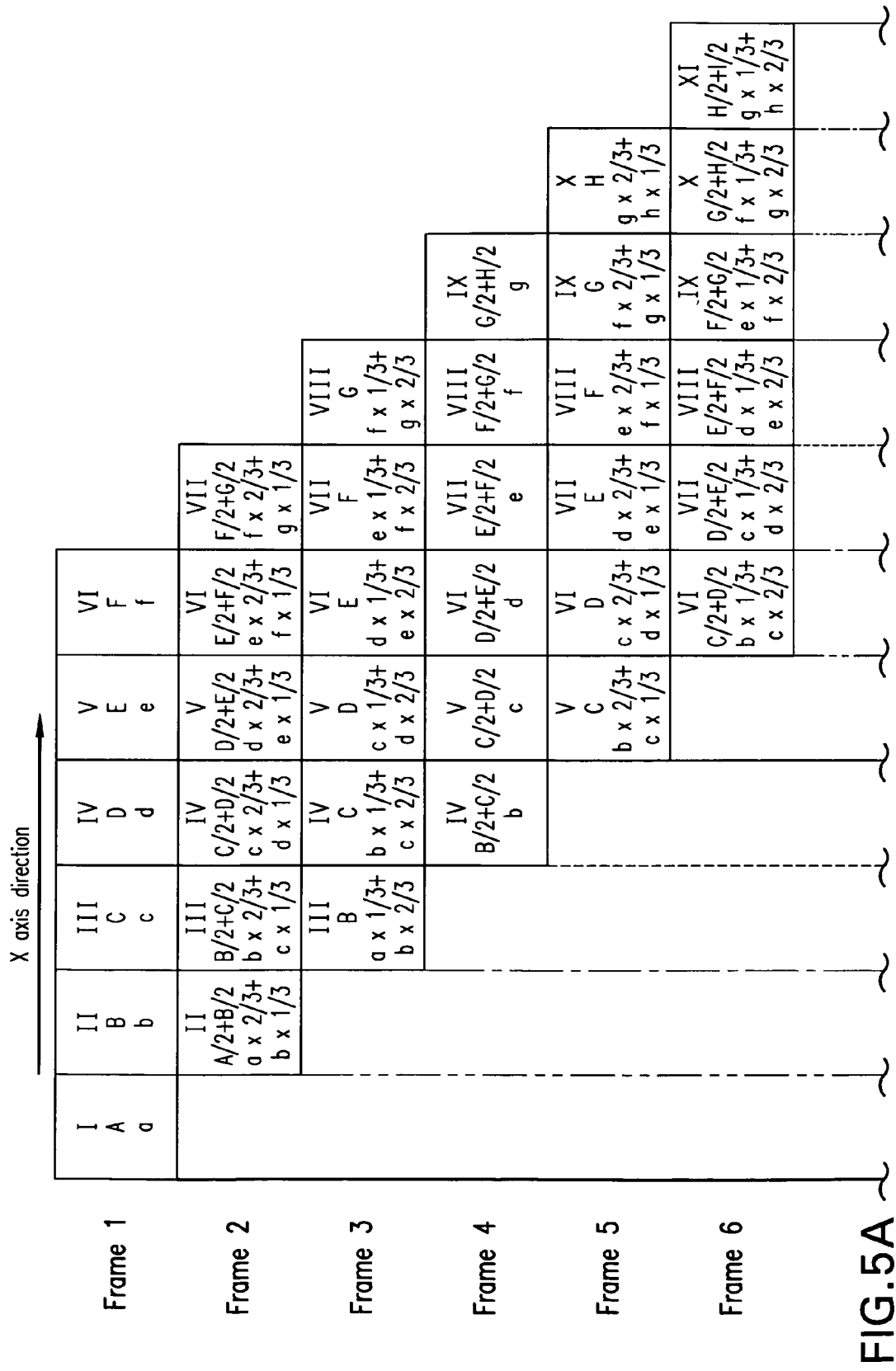
FIGS. 5A-5B collectively show an explanatory view showing whole frame images projected in the method of constructing multi-tomographic image of the prior application to the present invention.
Figure 5B:
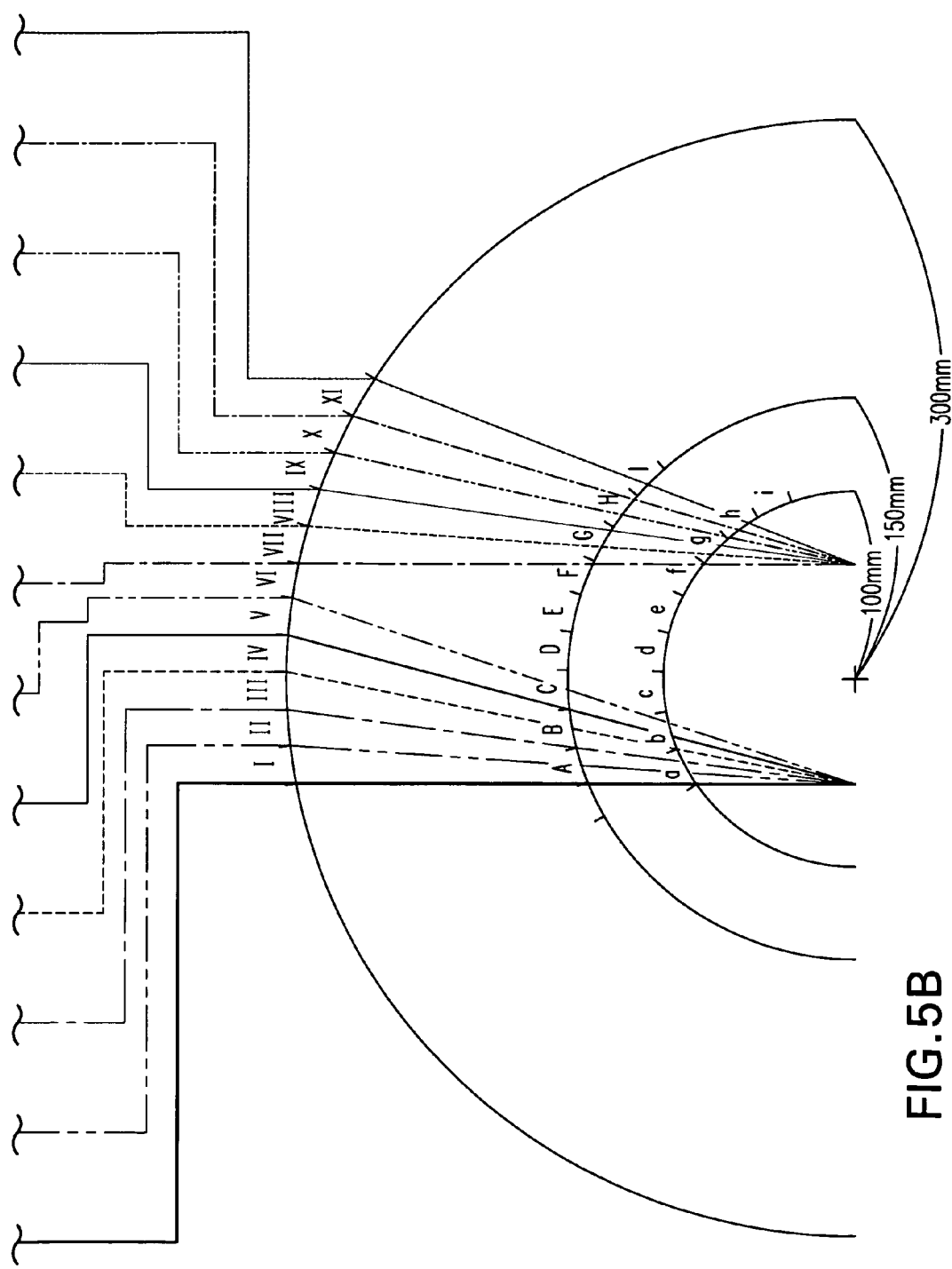
Figure 6:
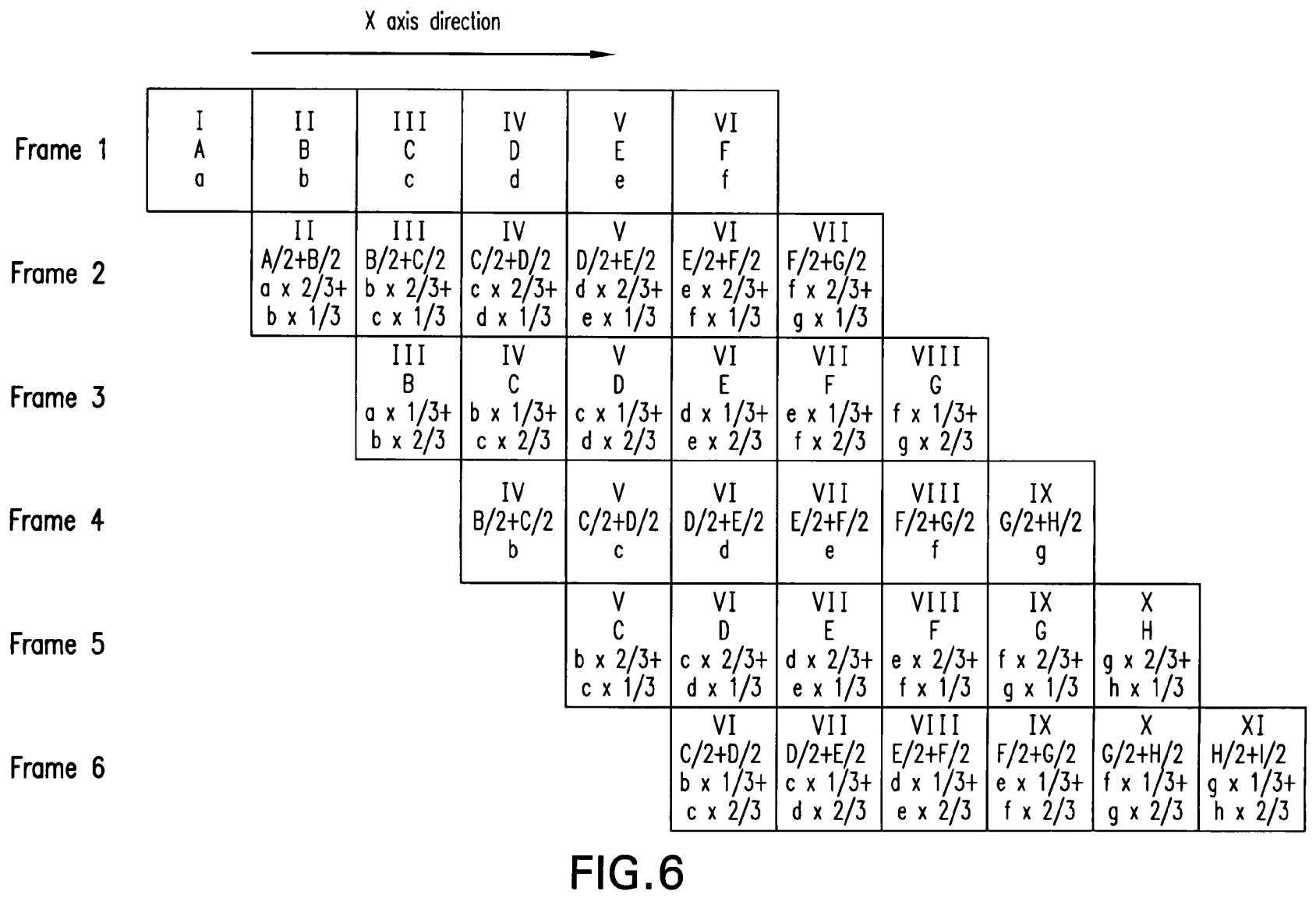
Figure 7A:
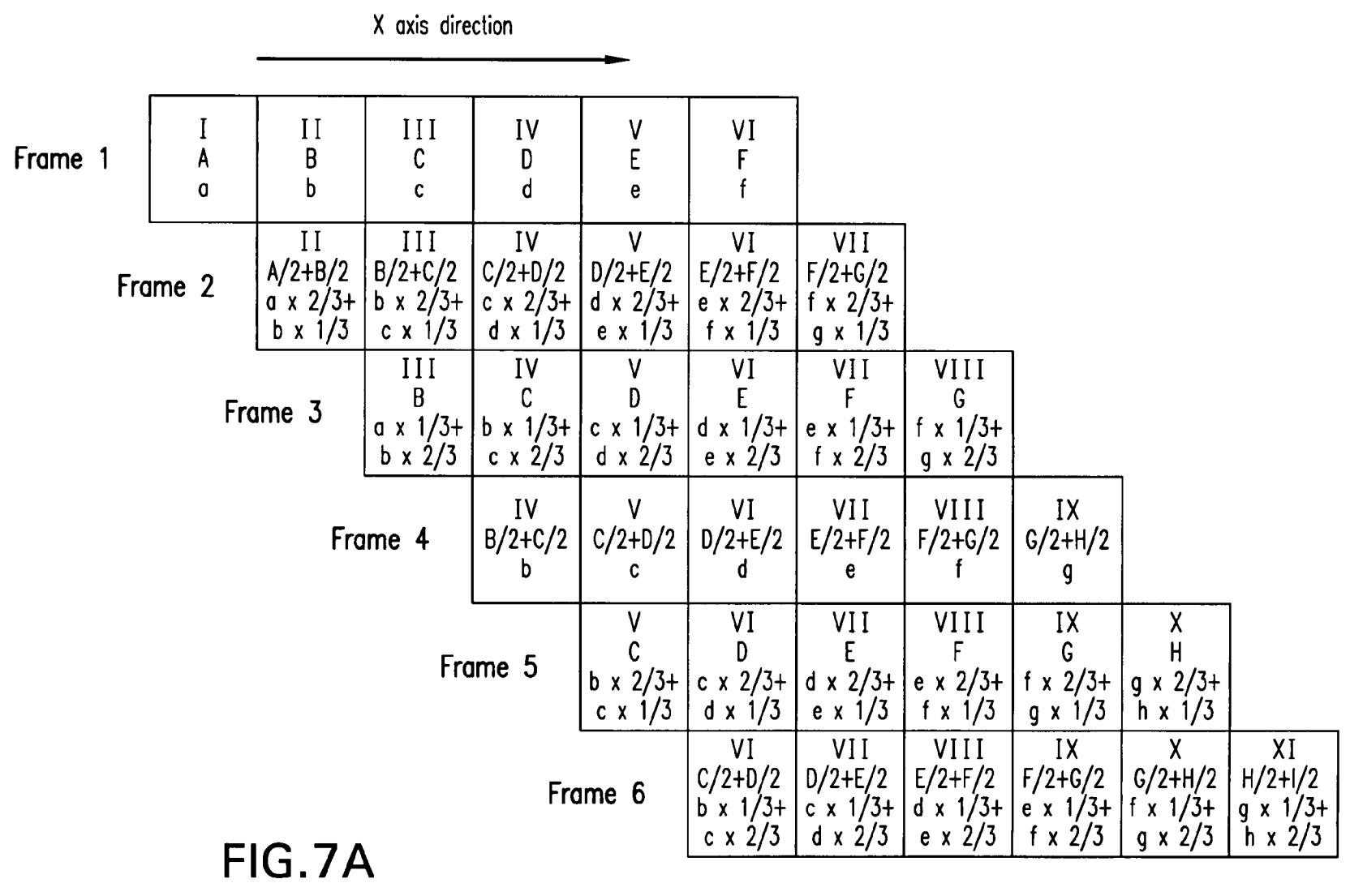
Figure 7B:
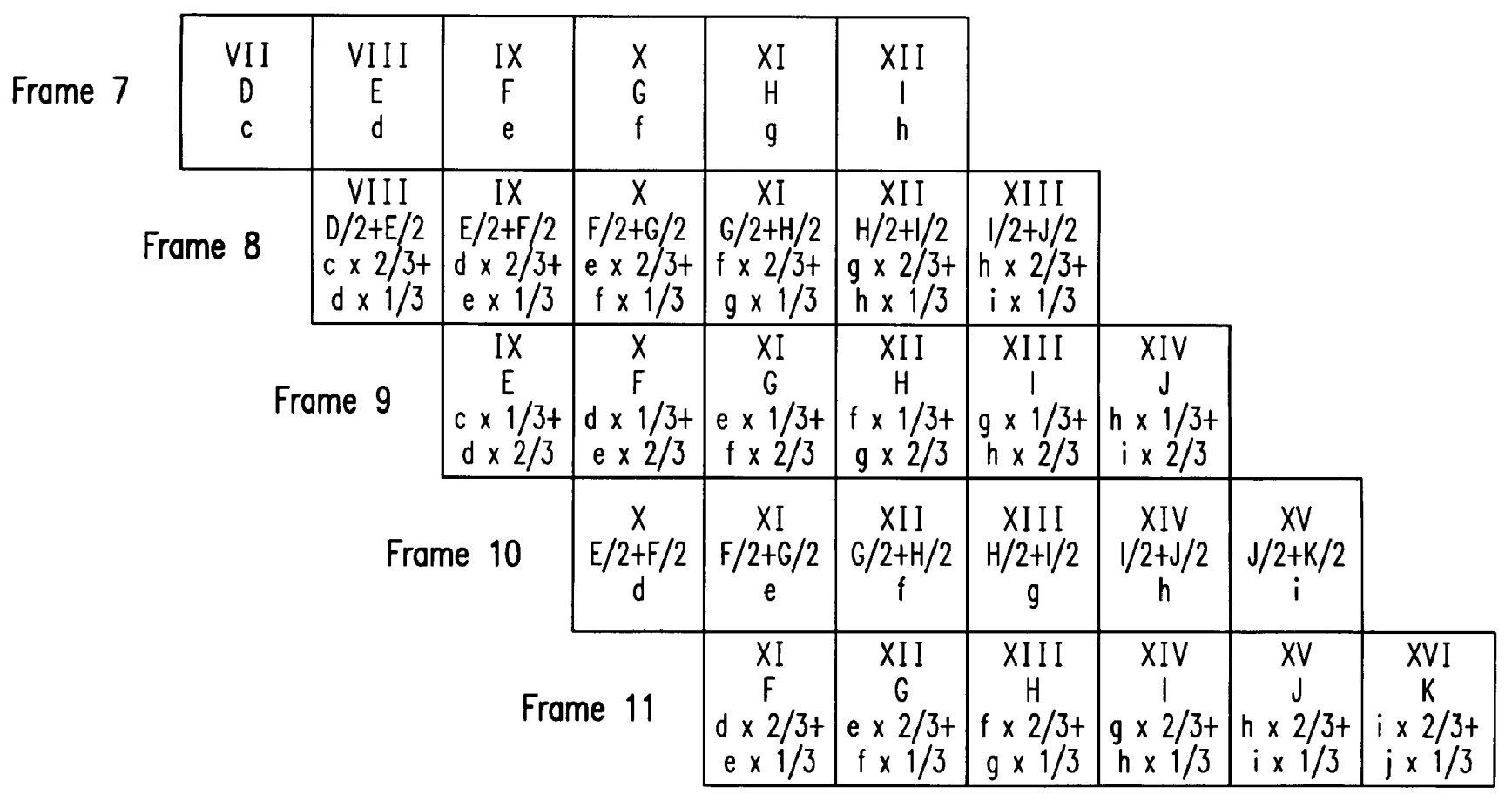
Figure 7D:
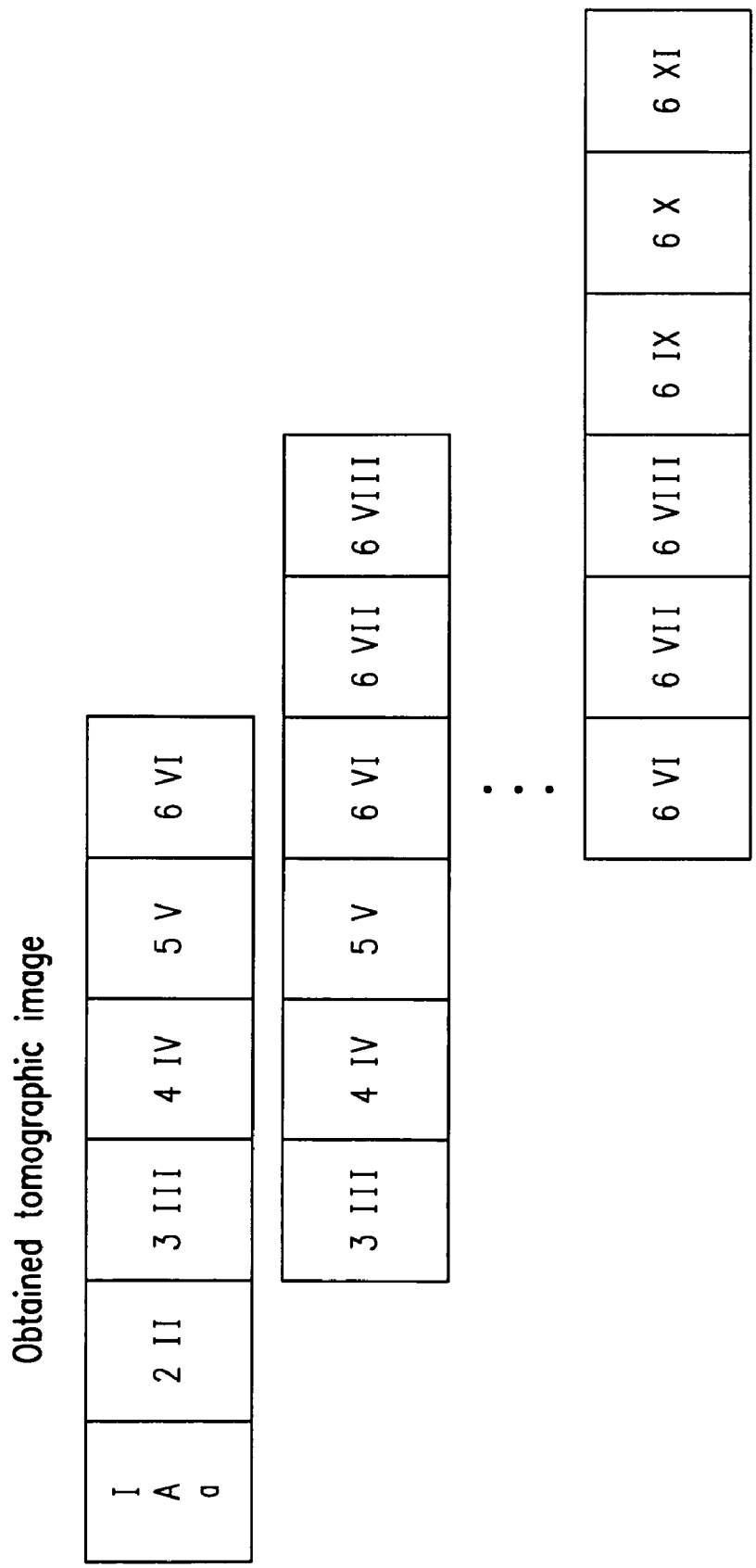

(1) Whole 18840 frame images stored in above large-capacity frame image storage means 6 are taken out, as shown in FIGS. 5 and 6, these frame images are overlapped by shifting the frame 1 and the frame 2 in the direction of X axis by one pixel unit of the CCD sensor, then according to the procedure of moving and overlapping frame 2 and frame 3 by one pixel unit of the CCD sensor, tomographic images obtained in case of shifting and overlapping 18840 frame images every one pixel of CCD sensor in order of X-ray photographing, become tomographic images of II, III IV, V, and VI (See FIG. 7), so that it is clear from FIG. 7 that thus obtained tomographic image is positioned on distance r=300 mm from the rotation center a.

Figure 8A:
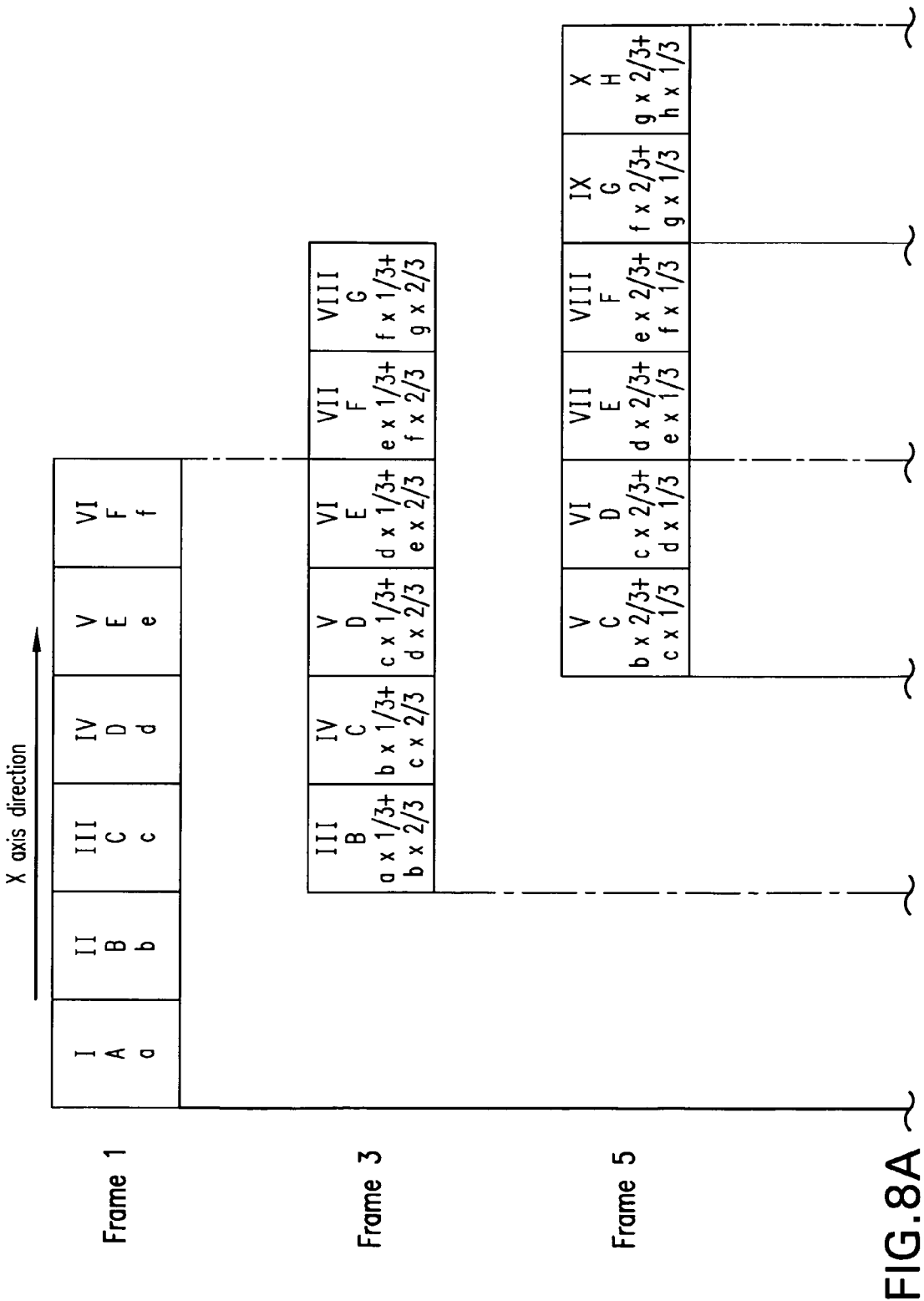
FIGS. 8A-8B collectively show is an explanatory view showing frame images every other frame projected by the method of constructing multi-tomographic image of the prior application to the present invention.
Figure 8B:
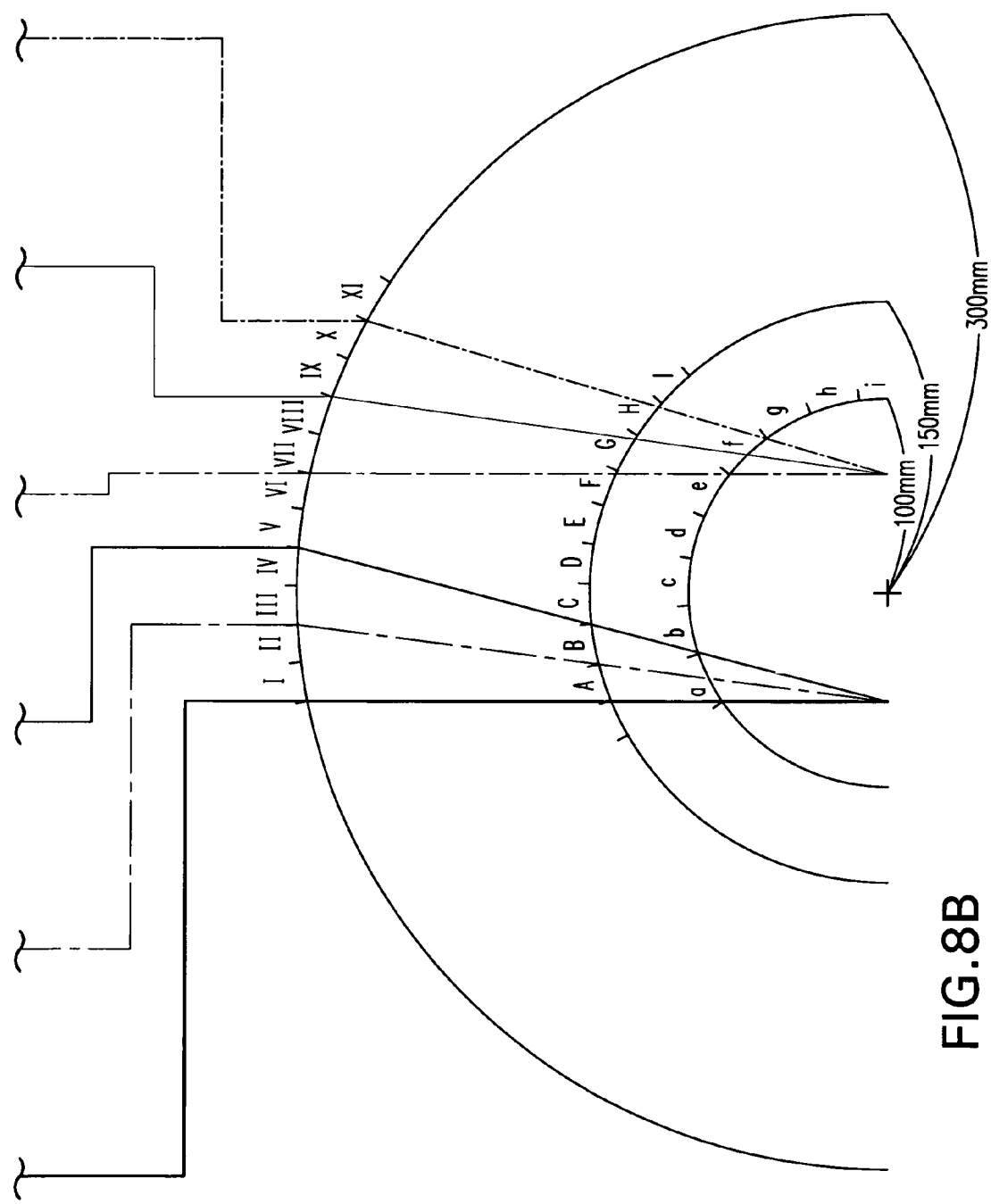
Figure 9:
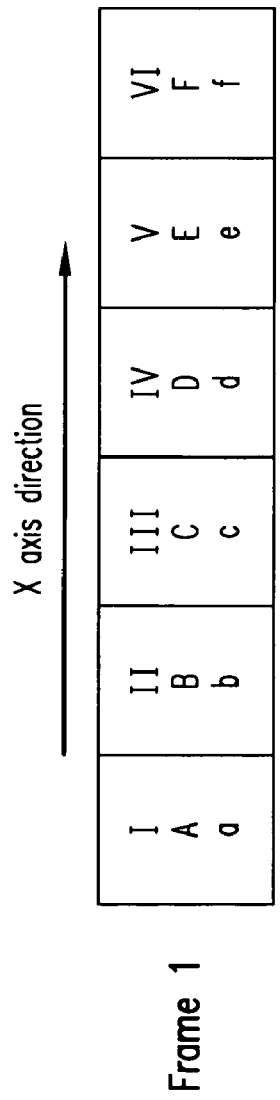
FIG. 9 is an enlarged detail of FIG. 8 showing frame images every other frame projected by the method of constructing multi-tomographic image of the prior application to the present invention.
Figure 10C:
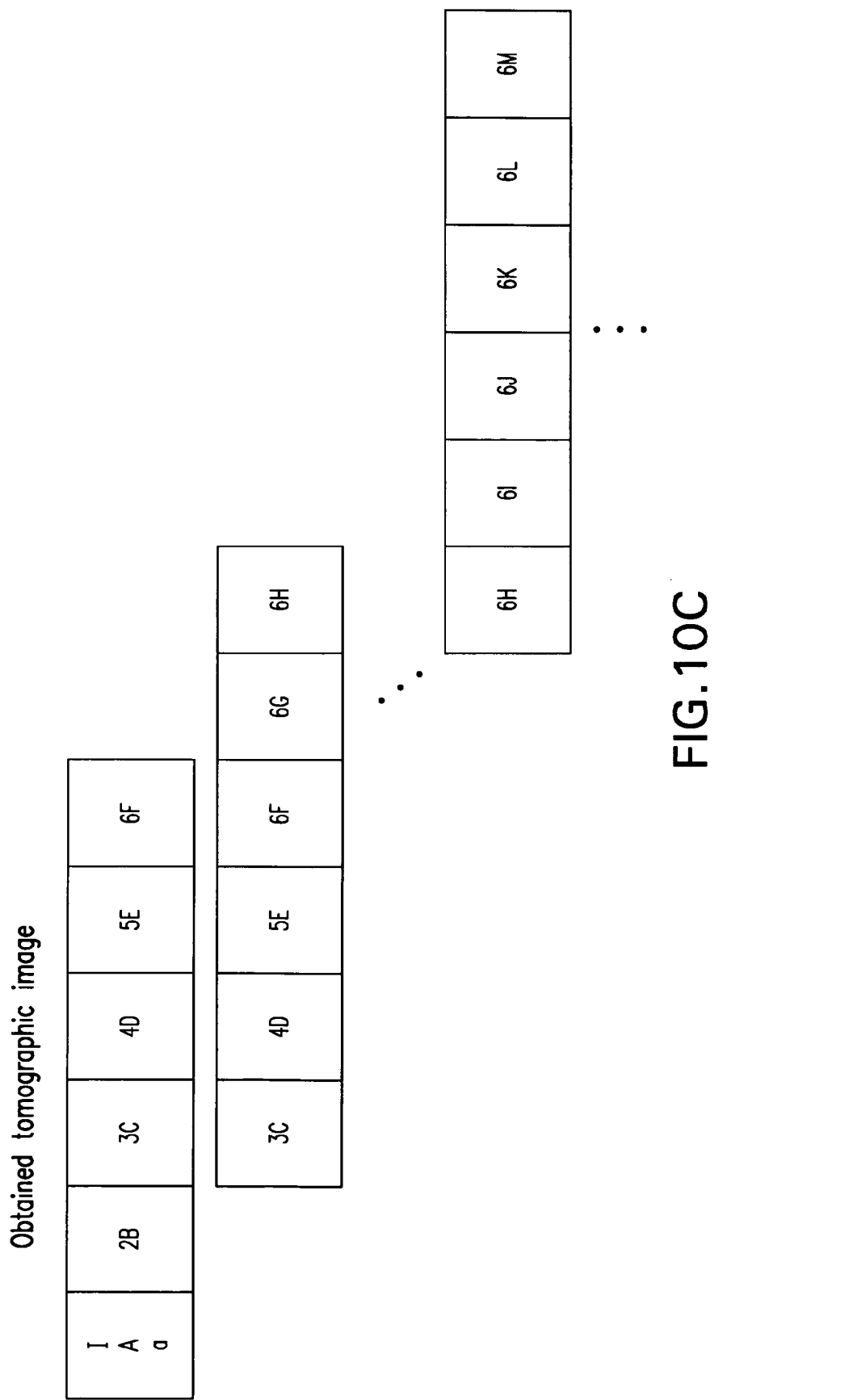

(2) Then, as shown in FIGS. 8A-8B and FIG. 9, as to the images of frame 1, frame 3, and frame 5 that taken out as a frame image every other frame (frame image shifted by two frames (two pixels)), from among the frame images (see FIGS. 5A-5B and 6) stored in the large-capacity frame image storage means 6, the frame 1 and the frame 3 thus taken out are shifted and overlapped in the direction of X axis every one pixel of the CCD sensor, and according to the procedure of shifting and overlapping the frame 3 and the frame 5 by one pixel unit of the CCD sensor, the tomographic images, that can be obtained in case of shifting and overlapping the frame images taken out of the large-capacity frame image storage means 6 by one pixel of the CCD sensor, become the tomographic images of B, C, D, E, and F as shown in FIGS. 10A-10C.

That is, every other frame of the frame images is taken out from 18840 frame images stored in the large-capacity frame image storage means 6, and in the case that shifts and overlaps every respective frame images thus taken out in the direction of X axis by one pixel unit of the CCD sensor, the frame sheet count in case of shifting and overlapping whole frame images by one pixel unit of the CCD sensor, becomes 18840×½, so that tomographic images B, C, D, E, and F thus obtained, become a tomographic image on the radius of r/2 (½ of radiuses r in case of shifting by one pixel with the use of first 18840 CCD sensors) that is a tomographic image in the radius of 150 mm.

Figure 11A:
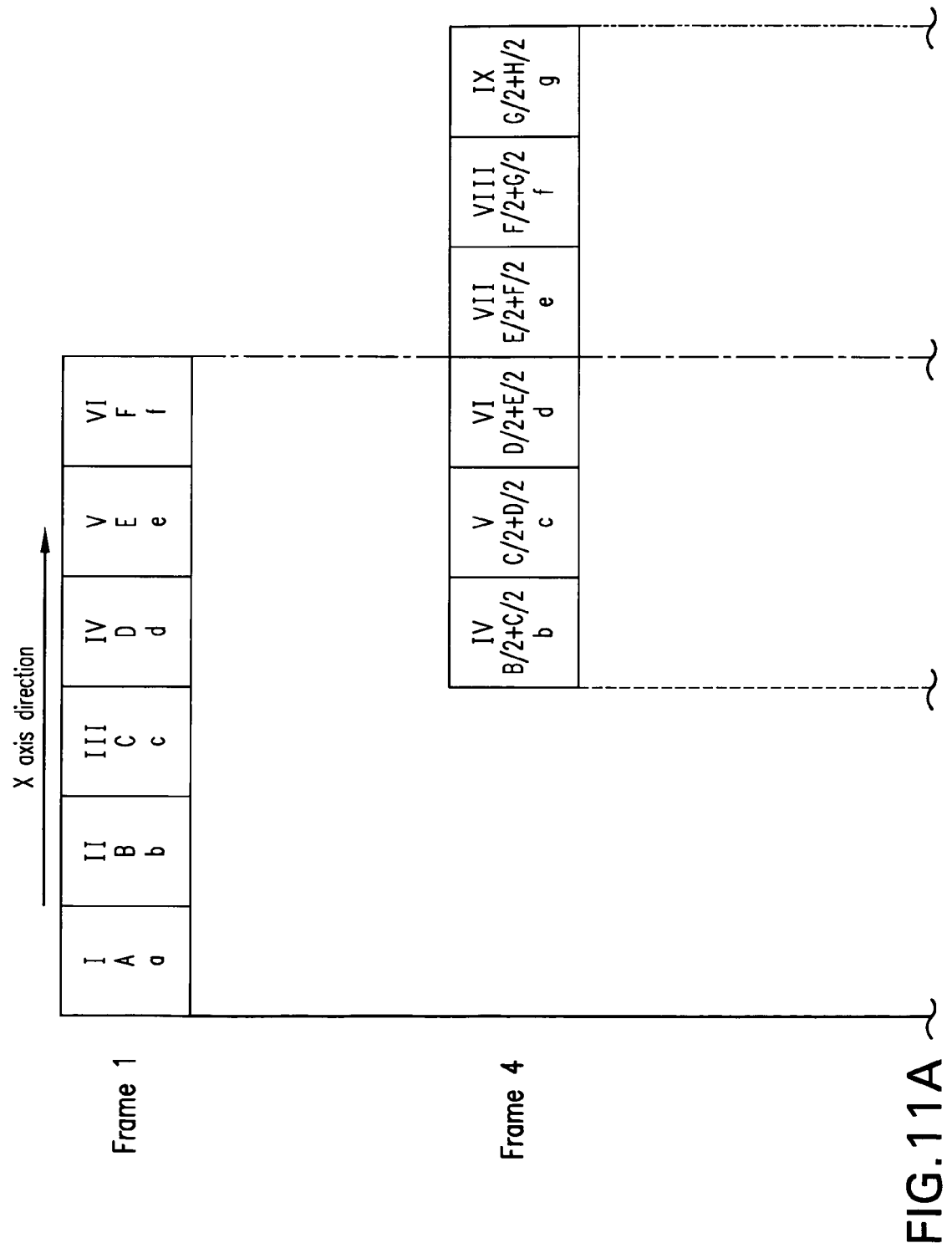
FIGS. 11A-11B collectively show is an explanatory view showing frame images every two frame projected by the method of constructing multi-tomographic image of the prior application to the present invention.
Figure 11B:
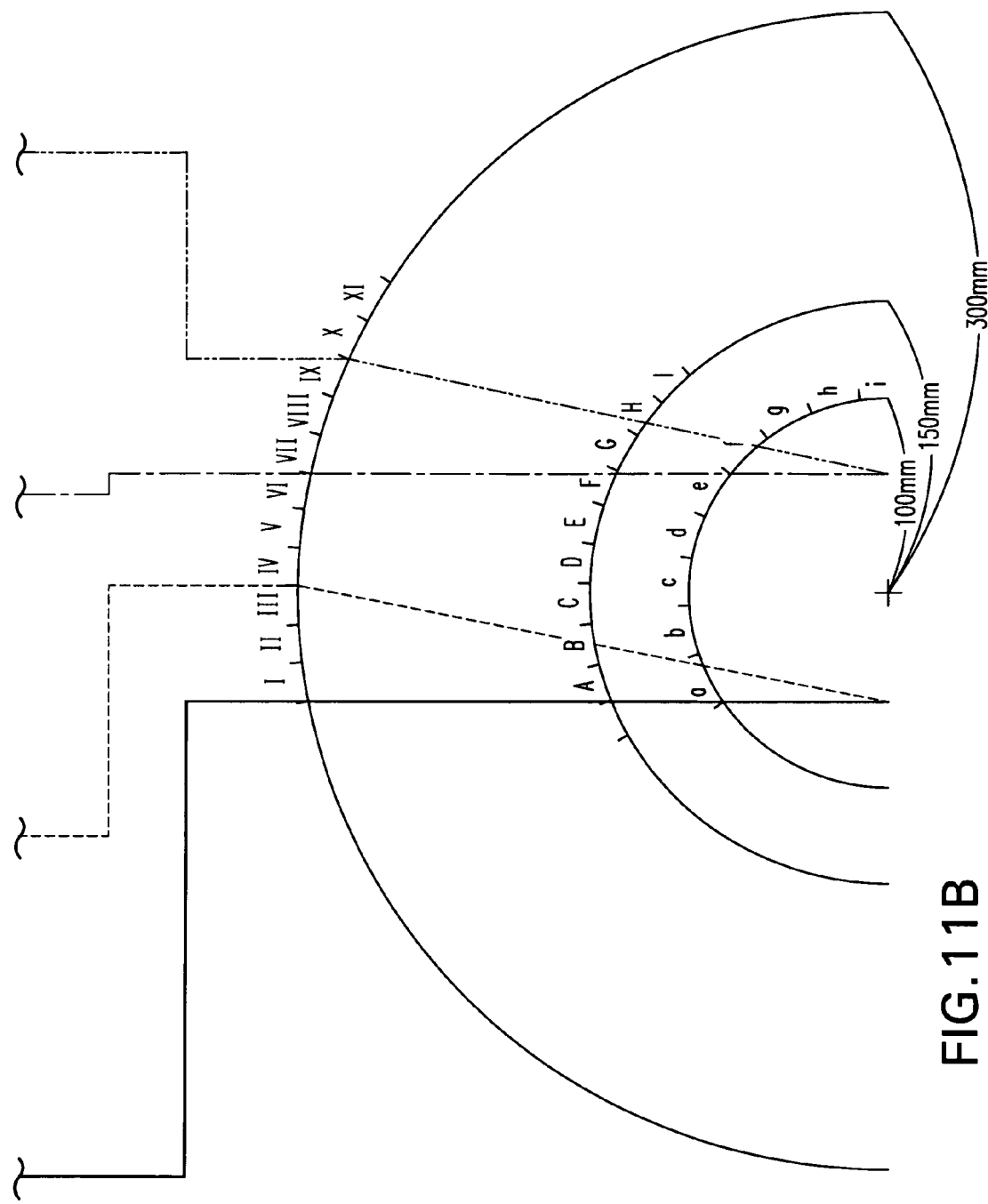
Figure 14:
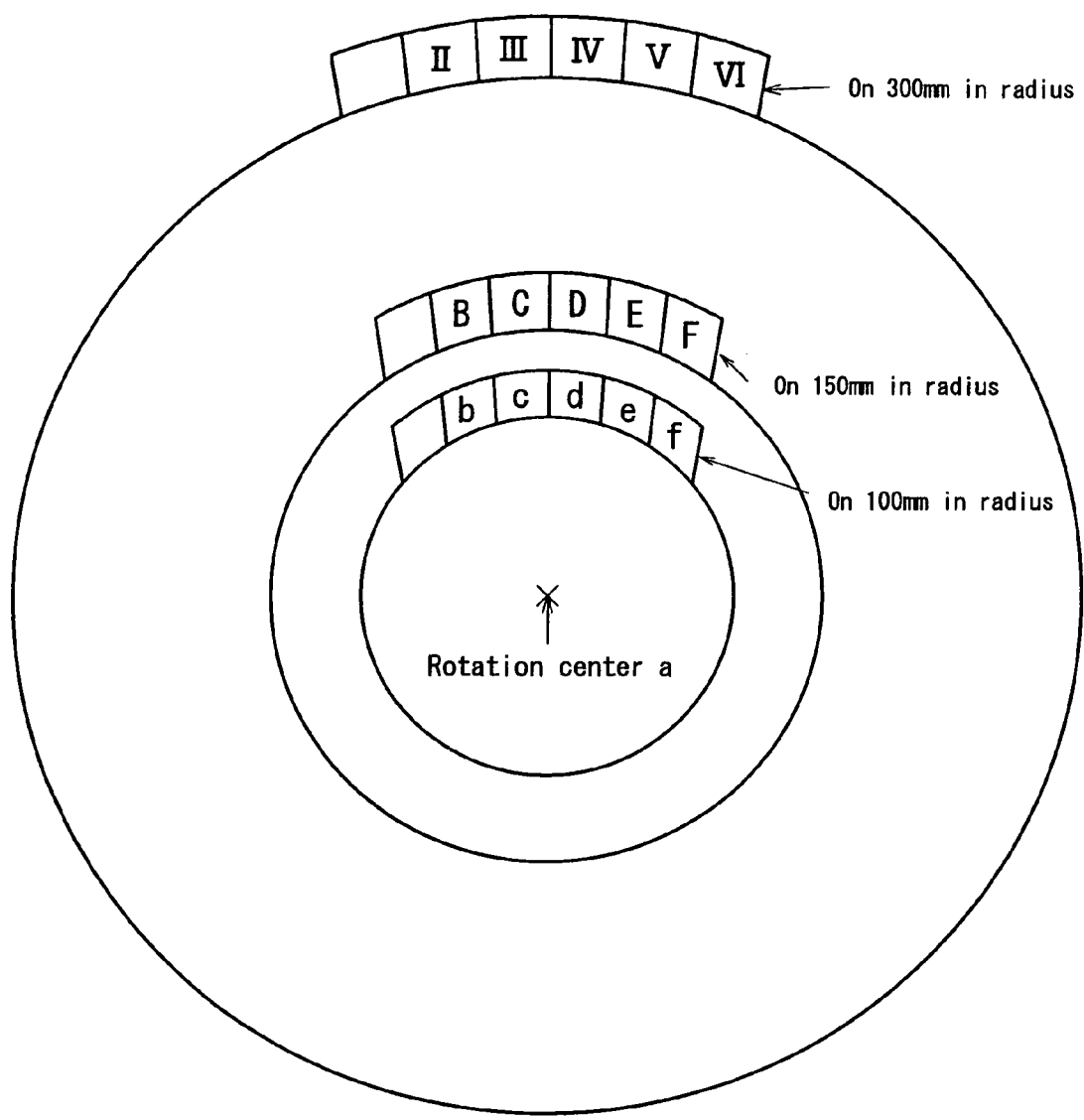
FIG. 14 is an explanatory view showing the tomographic image extracted by the frame-interlace method in the method of constructing multi-tomography of the prior application to the present invention.

(3) Then, from among the frame images (see FIGS. 5A-5B and 6) stored in the large-capacity frame image storage means 6 as shown in FIGS. 11A-11B and 12, frame 1 and frame 4, that include the frame images every two frames, (frame image shifted by three frames (three pixels)), are taken out, in the same way as in (1) and (2), according to the procedure of shifting and overlapping the frame 1 and the frame 4 thus taken out, in the direction of X axis by one pixel unit of the CCD sensor, the tomographic images, that can be obtained in case of shifting and overlapping the frame images taken out of the large-capacity frame image storage means 6 by one pixel unit of the CCD sensor, become the tomographic images of b, c, d, e, and f as shown in FIG. 13.

That is, in the case that shifts and overlaps respective frame images taken out of 18840 frame images stored in the large-capacity frame image storage means 6 every two frames, in the direction of X axis by one pixel unit of the CCD sensor, the frame sheet count in case of shifting and overlapping whole frame images by one pixel unit of the CCD sensor, becomes 18840×⅓, tomographic images b, c, d, e, and f, that can be obtained, become tomographic images on the radius of r/3, (⅓ of radiuses r in case of shifting by one pixel with the use of first 18840 CCD sensors), that is, on the radius of 100 mm.

That is, when respective frame images taken out every k frame out of respective frame images stored in the large-capacity frame image storage means 6 are shifted and overlapped in the direction of X axis by one pixel unit of the CCD sensor, the obtained tomographic images are positioned on the place r/k of radius r of the tomographic image obtained by shifting and overlapping whole frame images by one pixel unit of the CCD sensor.

Here, as an embodiment of the X-ray photographing principle of the present invention, it is assumed that the tomography positioned on the radius gyration 300 mm is photographed, sheet account of frame image stored in the large-capacity frame image storage means 6 is calculated, then the frame image is taken out every k frame out of respective frame images stored in the large-capacity frame image storage means 6, the radius gyration of the tomography obtained when the each frame image taken out is moved in the direction of X axis by one pixel unit of the CCD sensor and the sheet account of frame, that can be obtained, are calculated, the calculation result thereof is shown in Table 1.

TABLE 1

| Frame-interlace number | Sheet count of frame to be obtained (piece) | Turning radius (mm) |
|---|---|---|
| K = 1 (Whole frame images are used) | $n_1 = n_1/1 = 18840$ | $r_1 = 300$ |
| K = 2 (Every other frame image is used) | $n_2 = n_1/2 = 9420$ | $r_2 = r_1/2 = 150$ |
| K = 3 (Every two frame image is used) | $n_3 = n_1/3 = 6280$ | $r_3 = r_1/3 = 100$ |
| K = 4 (Every three frame image is used) | $n_4 = n_1/4 = 4710$ | $r_4 = r_1/4 = 75$ |
| K = 5 (Every four frame image is used) | $n_5 = n_1/5 = 3768$ | $r_5 = r_1/5 = 60$ |
| K = 6 (The frame image of putting five is used) | $n_6 = n_1/6 = 3140$ | $r_6 = r_1/6 = 50$ |
| K = 10 (Every nine frame image is used) | $n_{10} = n_1/10 = 1884$ | $r_{10} = r_1/10 = 30$ |
| K = 11 (Every ten frame image is used) | $n_{11} = n_1/11 = 1713$ | $r_{11} = r_1/11 = 27.27$ |
| K = 30 (Every 29 frame image is used) | $n_{30} = n_1/30 = 628$ | $r_{30} = r_1/30 = 10$ |
| K = 31 (Every 30 frame image is used) | $n_{31} = n_1/31 = 608$ | $r_{31} = r_1/31 = 9.68$ |

That is, in the image construction according to the frame interlace method, the radius gyration in the position of tomographic image obtained from n frame images, that is, assuming that the radius gyration from rotation center a is to be r, and the frame images are extracted by every k frame, in the position of tomographic image obtained by moving and overlapping each frame image thus taken out in direction of X axis by one pixel, becomes r/2, r/3, and ... respectively. However, as is clear from FIG. 11, it is impossible to extract respective tomographic images between radii r and r/2, between radii r/2 and r/3, .... Further, in order to obtain the tomographic image that the interval of the radius gyration is made a slight distance, the frame images taken out every 30 frames in the direction of X axis from among respective frame images stored in the large-capacity frame image storage means 6, is used, the frame images should be overlapped by one pixel unit of the CCD sensor, but, the radius gyration at this time becomes about 10 mm.

Thus, in the image construction according to the frame interlace method, if the interval of reproduced radius gyration r should be detailed, the radius gyration of the tomography that can be obtained by one photographing can be taken very large, the tomography at fine interval of the radius gyration can be obtained by enlarging the interlace interval when the frame is taken out. However, it was confirmed that in this case, the radius of gyration becomes small, so that covering of required diagnosis region (for example, dental arch region) becomes difficult.

Moreover, if the CCD sensor used in the above frame interlace method is utilized as it is, the features of making the radius gyration large and of performing large frame interlace method result in a decrease in the number of sheets of the frame images used for overlapping, and thus the image with tomographic effect can not be obtained. In addition, it was confirmed that there are some problems, in which if the outer periphery of suit is set, as in the above calculation, even though the tomographic image can be obtained on the interval of a necessary radius, the radius gyration thereof is too small to supply it to practical use, or so.

Therefore, only in the image construction according to the frame interlace method, it is difficult to obtain the tomographic image that can be provided to the clinical diagnosis.

Figure 15:
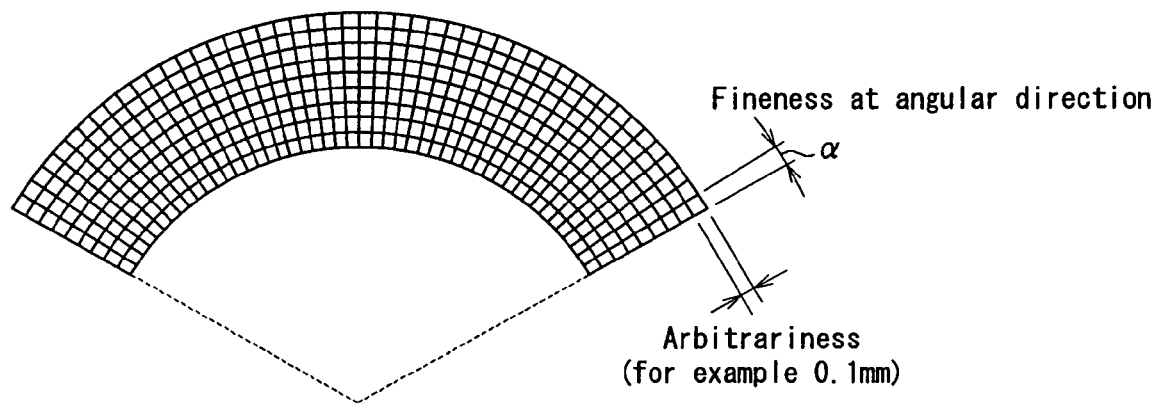
FIG. 15 is an explanatory view showing a circular arc fineness by which the photographed image of the present invention is arranged.

Then, according to the present invention, the tomographic images in a plurality of radius locations are obtained in one-time X-ray photographing, a lot of information on the diagnosis are provided by forming the stereoscopic image with these obtained tomographic images, so that, as shown in FIG. 15, comparing with the prior art, the thickness of radial and the fineness of the angular direction of the tomographic image that can be obtained herein, can be set and adjusted arbitrarily, and thus further imperceptible stereoscopic image can be obtained.

Second Embodiment

According to the present invention, the square cell elements expressed by spherical coordinates are arranged in the form of substantial circular arc at the radius location of desired extracting place, and value of each pixel is projected and arranged onto the square cell element along the x-ray penetration route at the X-ray photographing. This process is performed to the X-ray photographed image at each divided unit angle respectively by using the angle that rotates an X-ray photographing system (X-ray source and receptor) to the subject while obtaining respective photographed images, as unit angle $\Delta\theta$, and the tomographic image in the radius location of the desired extracting place can be obtained by shifting respective photographed images every respective unit angles and adding them sequentially.

Figure 16:
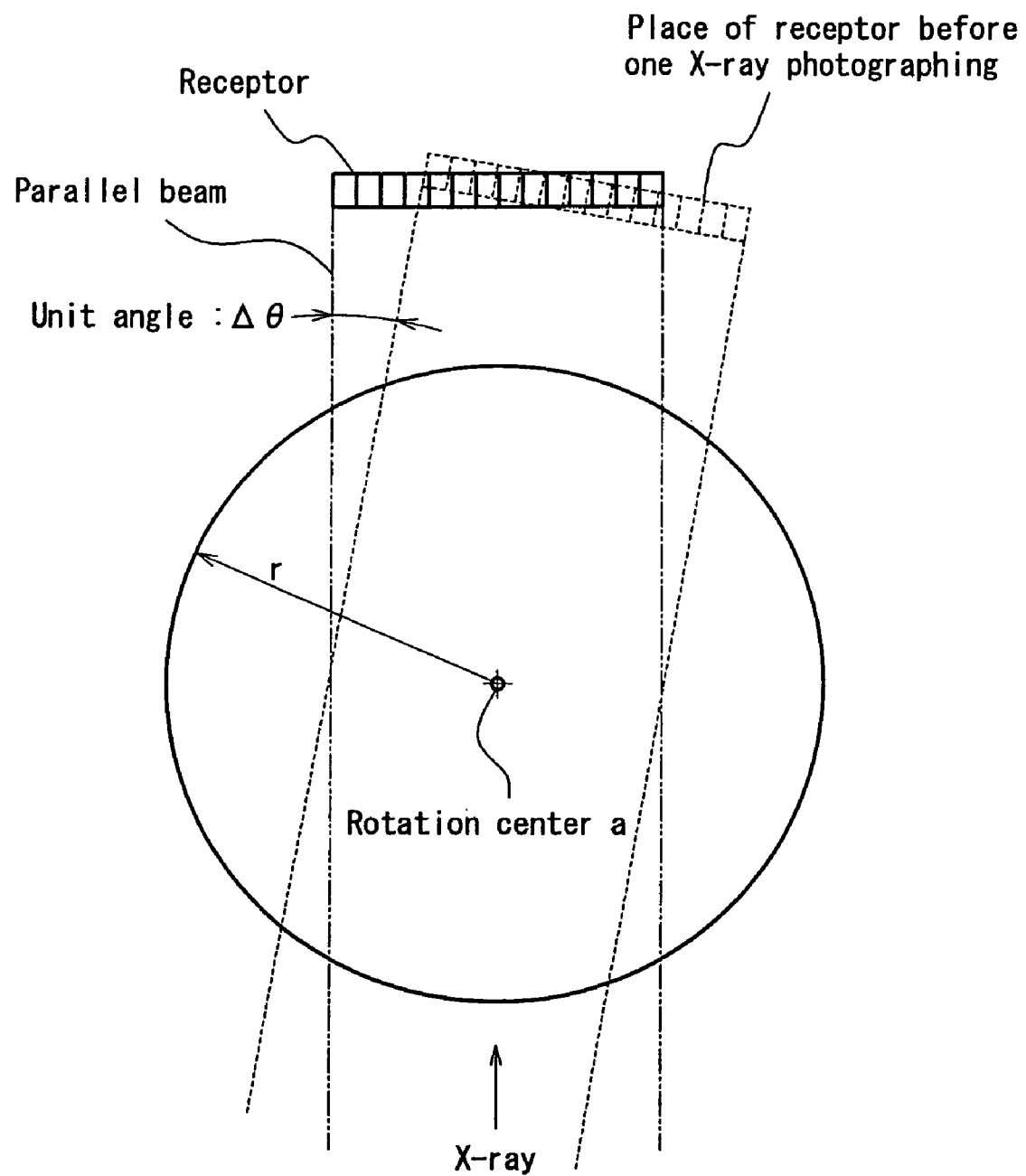
FIG. 16 is an explanatory view showing the state of the radiography of the method of constructing multi-tomography according to the present invention.

In the present invention, the pixel of the photographed image is obtained in a circular orbit as shown in FIG. 16. That is, in the same way as in the case explained in FIG. 4, the subject is arranged at the rotation center a, and a parallel X-ray beam is irradiated from the X-ray source (not shown) to the subject, and the photographed image is recorded to linearly-arranged receptor, being the X-ray imaging means arranged behind the subject. In this case, it is assumed that the X-ray photographing system (X-ray source and receptor) is rotated on the subject every unit angle $\Delta\theta$ to photograph the radiogram.

Figure 17:
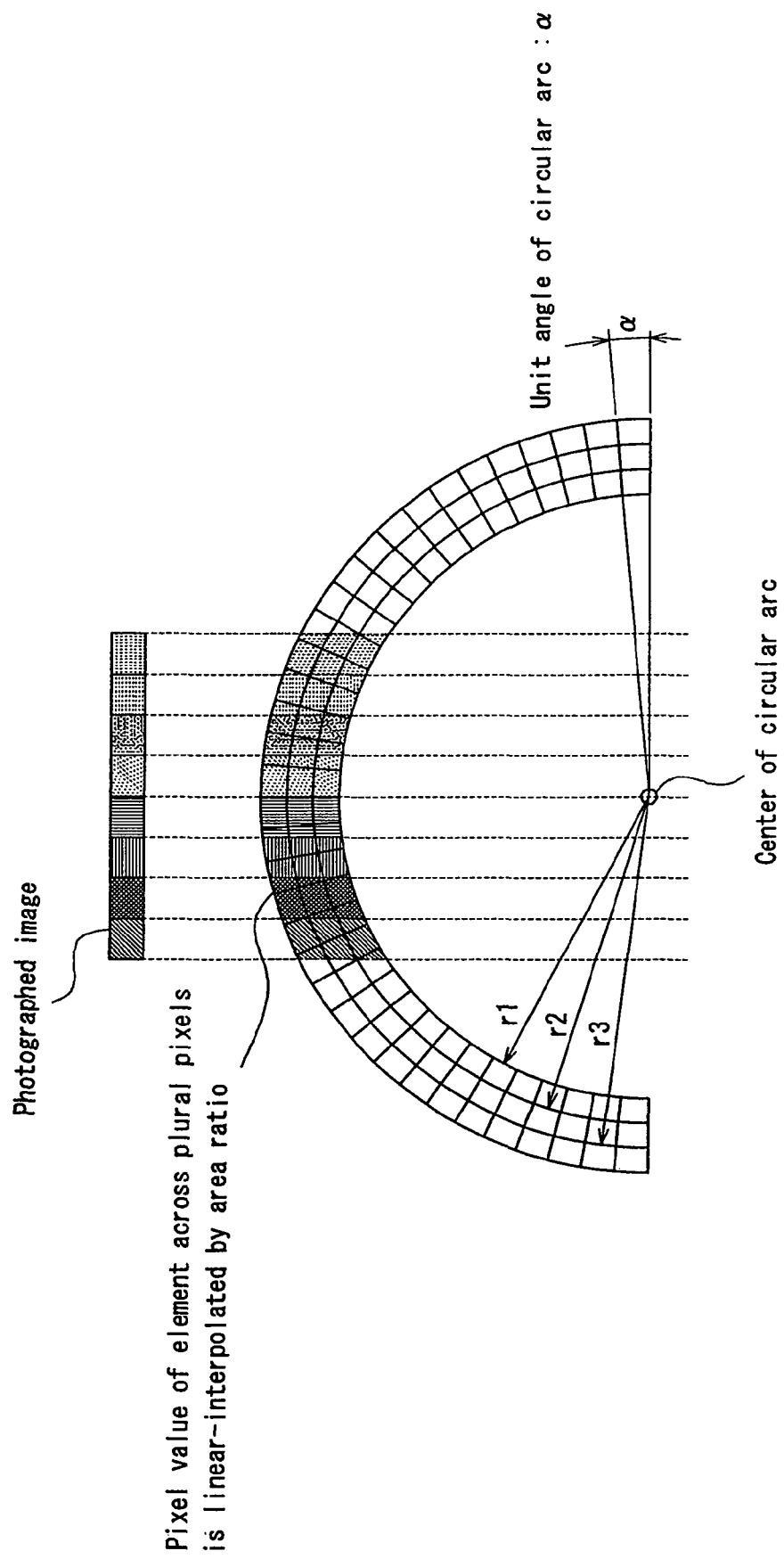
FIG. 17 is an explanatory view showing whole frame images projected in the method of constructing multi-tomographic image according to the present invention.

In this way, as shown in FIG. 17, pixels thus obtained of linearly arrayed photographed images are converted into square cell elements arranged in the form of circular arcs of radii r1, r2 and r3, respectively, as an element of a circular arc pixel. In this case, the pixel value of an element across plural pixels in relation to the respective square cell elements is linearly interpolated by area ratio. In this way, pixels of photographed image arranged in straight can be projected onto the square cell elements arranged in circular arc.

The process similar to described above is performed as to all of the photographed images in respective angles, thereby constituting an array of elements arranged like circular arc by the projection.

Figure 18:
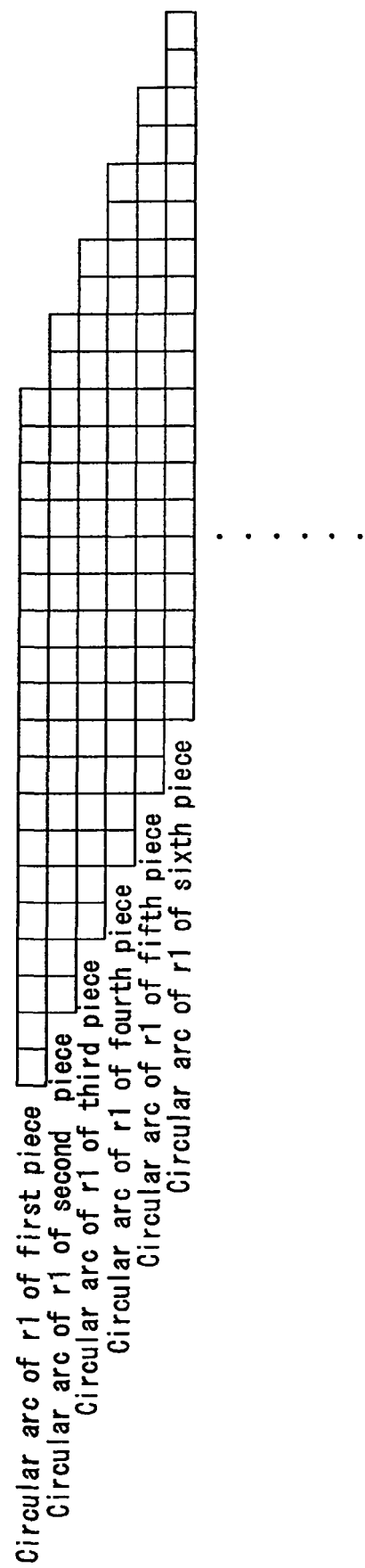
FIG. 18 is an enlarged detail of FIG. 5 showing whole frame images projected in the method of constructing multi-tomographic image according to the present invention.

Now, assuming that $\Delta\theta$ is a rotating unit angle of X-ray photographing system (X-ray source and receptor) that is rotated about the subject when photographed images of respective frames are obtained, and $\alpha$ is a unit circle arc angle of a circular arc array element, as shown in FIG. 18, pixel values (area) on the circular arc of radius $r_1$ that exists only by the X-ray photographing frame sheet count arranged in the form of the circular arc while shifting every ratio $\Delta\theta/\alpha$ of unit angle, are added. In this way, the tomographic image in radius location $r_1$ can be constructed. For example, in the case of ratio $\Delta\theta/\alpha=2$ of unit angle, as shown in FIG. 18, respective frame elements are added by shifting the pixel by two pixels, respectively.

As to the circular arc of radius $r_2$ and circular arc of radius $r_3$, by adding the pixel in the same way as in the case shown in FIG. 18, the tomographic images on radius locations $r_2$ and $r_3$ can be constructed.

Figure 19:
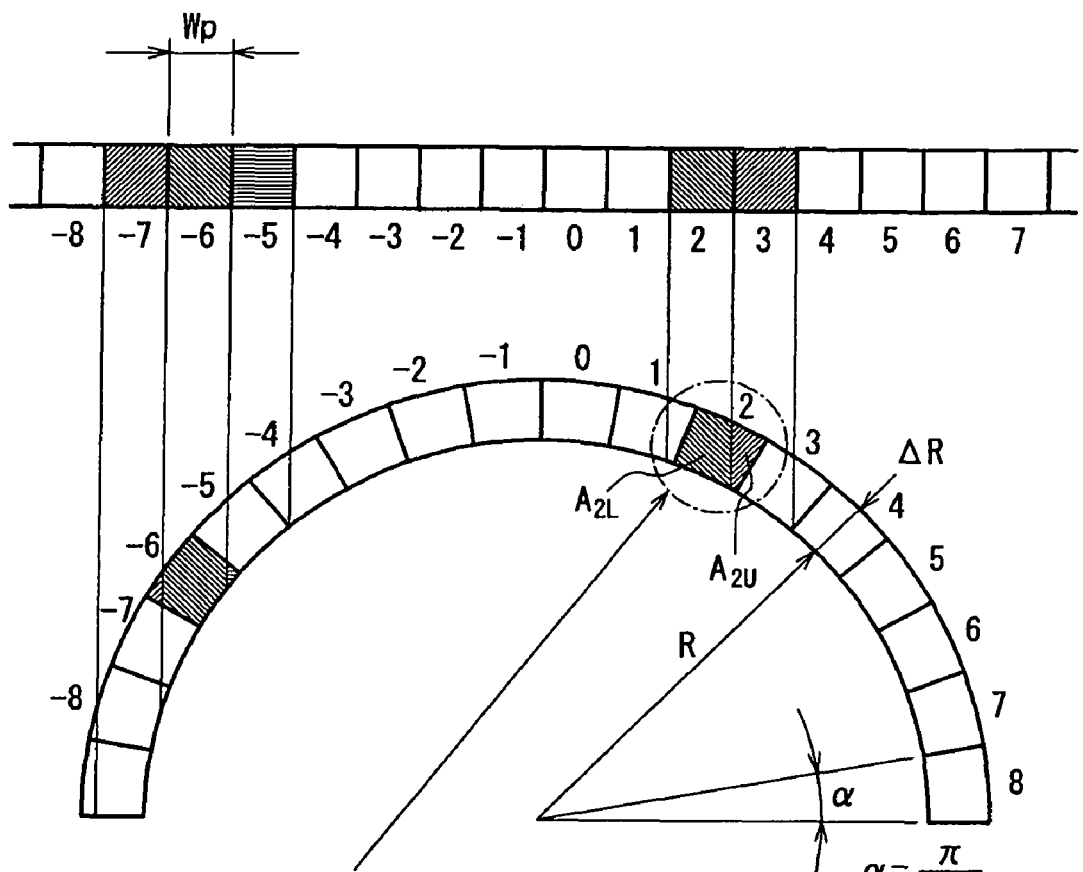
FIG. 19 is an explanatory view of conversion calculation to a circular arc array element in the method of rearranging the photographed image of the linear array into a form of circular arc.

In this way, means for converting the element across plural pixels into a circular arc array is explained in FIG. 19. by linear-interpolating the pixel value by the area ratio.

In the present invention, a following calculation approach is established as a method of rearranging the photographed image of the linear array in the form of circular arc.

As shown in FIG. 19, a region enclosed with semicircle of inside radius R and outside radius R+$\Delta$R is divided into $N_R$ piece. Respective pixels LE (−8, −7, ..., 0, ... +7, +8) of photographed images of linear array are projected onto elements RE (−8, −7, ..., 0, ... +7, +8) of circular arc array in parallel. At this time, plural pixel number $X_D(X_A,i)$ and the number $N_D(X_A,i)$ of linear pixels LE that enter elements of $X_A$ th of circular arc array, or an area ratio $C_D(X_A,i)$, to which these pixels occupy the region of circular arc array element RE, are calculated. A circular arc conversion table at radius R to the value of the respective pixels of linear photographed image calculated in this way, is constituted.

In this way, the formula, that converts the photographed image of the linear array into a circular arc array, is represented by following expression (1).

$$P_A(X_A) = \sum_{i=1}^{N_D(X_A)} C_D(X_A, i) P_D(X_D(X_A, i)) \quad (1)$$

$$\left( \sum_{i=1}^{N_D(X_A)} C_D(X_A, i) = 1 \right)$$

In the above expression (1), $P_A$ represents pixel value converted into a circular arc array, and $P_D$ represents pixel value of the photographed image.

After converting whole photographed images into a circular arc array by the expression (1), whole photographed images are overlapped while shifting only $S_A$. Herein, $S_A$ is a value that could be obtained from angle that rotated X-ray photographing system to the subject while respective photographed images are obtained, and number $N_R$ of divided elements of circular arc array, by following expression (2).

$$S_A = \frac{\Delta \theta \cdot N_R}{\pi} \quad (2)$$

$S_A$ is a value that does not depend on the radius of a circular arc array, so that the same equation can be used to calculate overlapping as to a circular arc array of a different radius.

The tomographic image in the place from radius R to radius R+ΔR can be obtained by the calculation as far as here. After obtaining a plurality of tomographic images by changing R to $R_0, R_1=R_0+R, R_2=R_1+R, R_3=R_2+R,$ and ..., these images are bent in the form of circular arc of the radius corresponded to these images, respectively, thereby arranging in the three dimensional shape.

In FIG. 19, $W_P$ shows pixel size of the photographed image, $A_{2L}$ shows the area in which the second pixel of the photographed image occupies the region of the second element of circular arc array, and $A_{2U}$ shows the area in which the third pixel of the photographed image occupies the region of the third element of circular arc array.

In the above embodiment, for the sake of convenience, pixels of photographed image arranged linearly are be projected onto the square cell elements arranged in the shape of circular arc but, the present invention is not limited thereto and pixels of photographed image arranged linearly can be converted into the square cell elements of not only circular shape, but also elliptic shape and the row of teeth shape.

In this way, by performing a summation shown in FIG. 18, the tomographic images in radius locations $r_2$ and $r_3$ consequently, the multi-tomographic image photographing can be constructed, further, the stereoscopic image of whole diagnosis region can be obtained by slicing the multi-tomographic image thus obtained in a transverse direction and using a volume rendering software. As such a volume rendering software, commercial software, or an original software can be used.

Figure 20A:
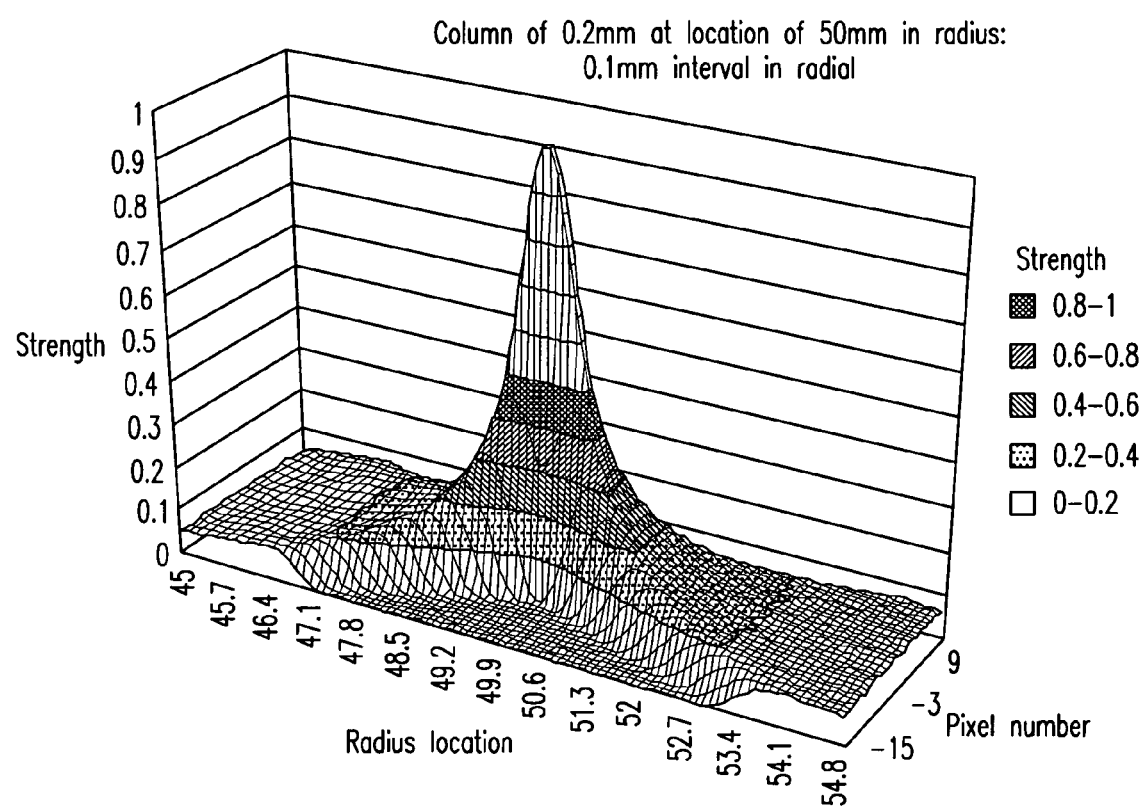
FIGS. 20A-20C show a perspective view, a top plan view, and a cross-sectional view wherein in a method of constructing multi-tomographic image of the present invention, under the conditions that puts the column of 0.2 mm at location of 50 mm in radius and photographs, intensity distribution when circular arc array is provided in radial at intervals of 0.1 mm to construct multi-tomographic image, is shown on the pixel number 0, respectively.
Figure 20B:
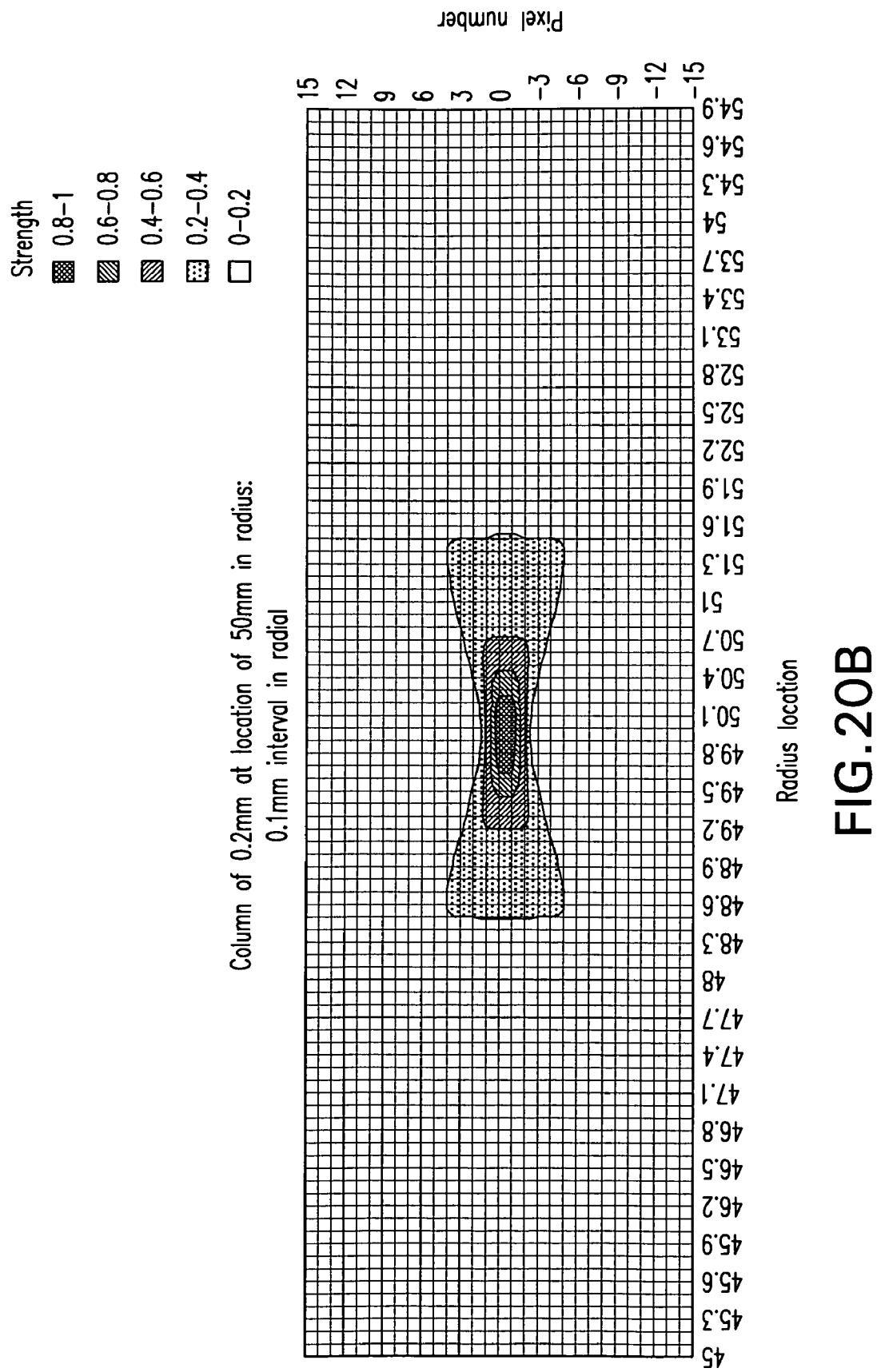
Figure 20C:
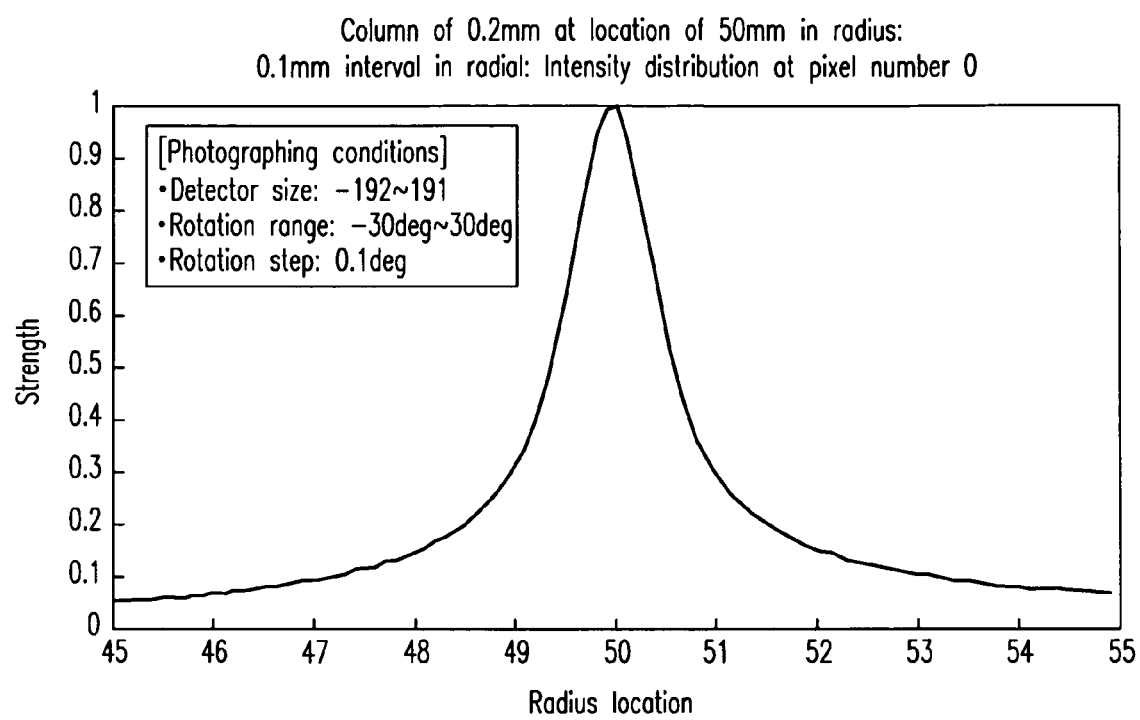

In the method of constructing multi-tomographic image of the present invention, as described above, under the conditions that puts the column of 0.2 mm at location of 50 mm in radius and photographs, intensity distribution when circular arc array is provided in radial at intervals of 0.1 mm to construct multi-tomographic image, is shown in FIGS. 20A-20C by perspective view, top plan view, and cross-sectional view on the pixel number 0, respectively.

Figure 21A:
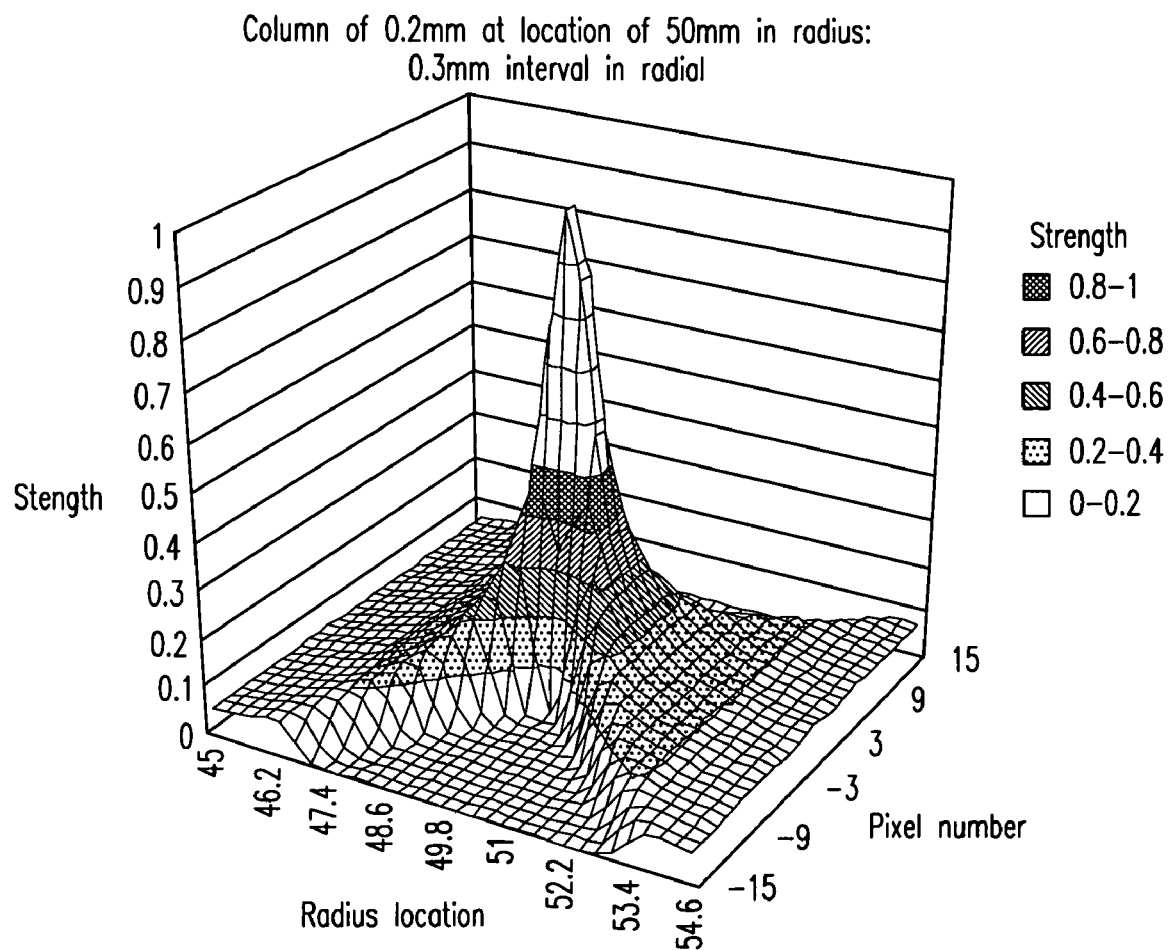
FIGS. 21A-21C show a perspective view, a top plan view, and a cross-sectional view wherein similarly, under the conditions that puts the column of 0.2 mm at location of 50 mm in radius and photographs, intensity distribution when circular arc array is provided in radial at intervals of 0.3 mm to construct multi-tomographic image, is shown on the pixel number 0, respectively.
Figure 21B:
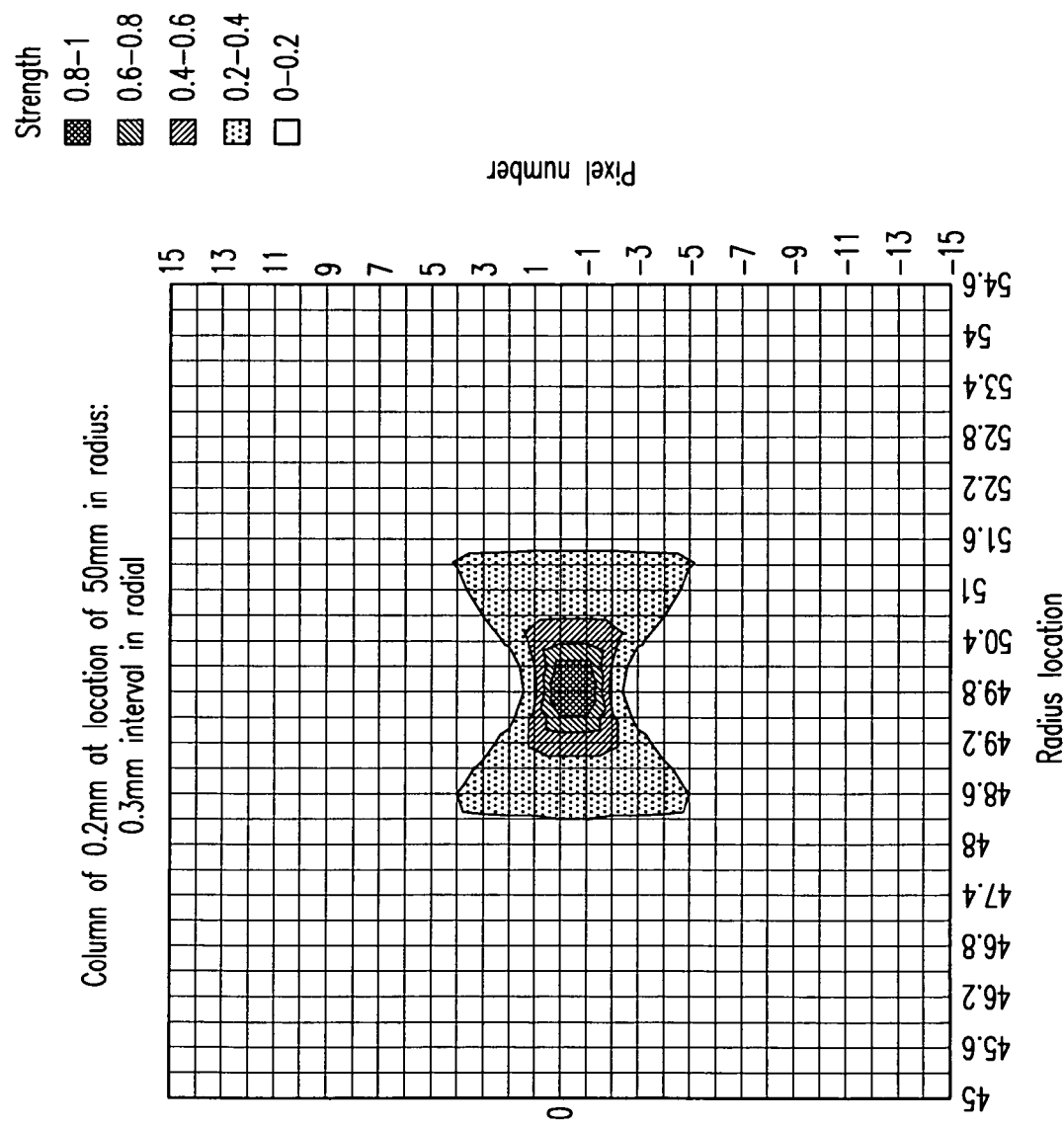
Figure 21C:
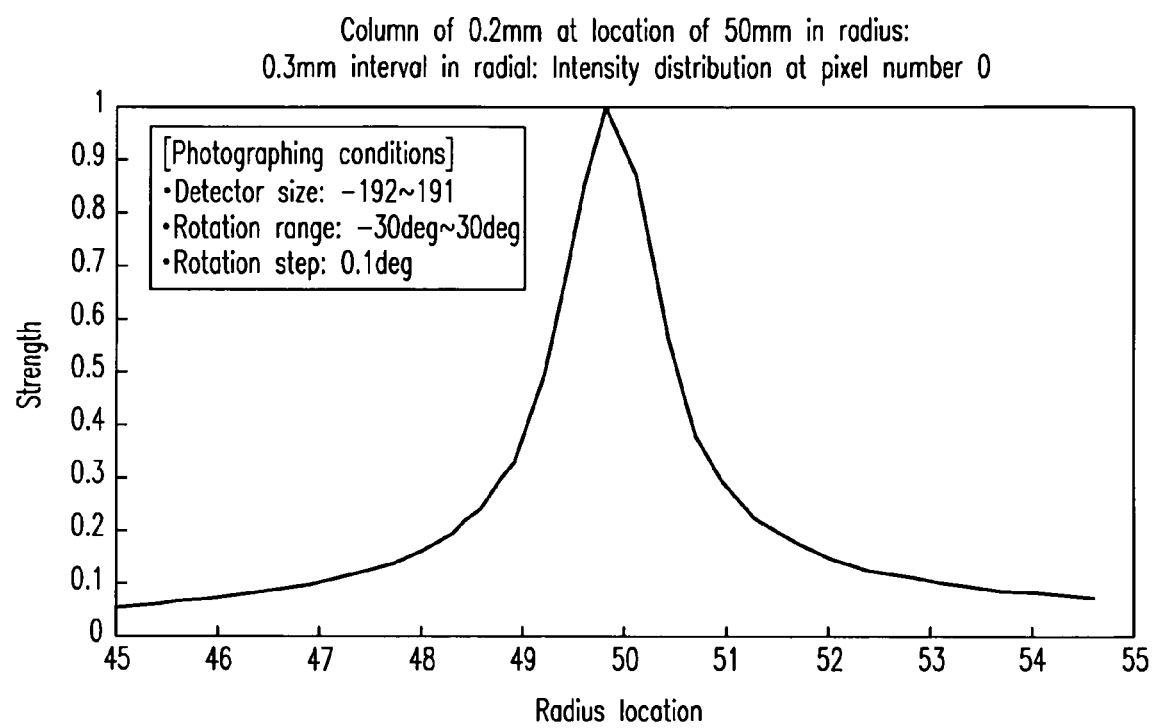

In the method of constructing multi-tomographic image of the present invention, as described above, under the conditions that puts the column of 0.2 mm at location of 50 mm in radius and photographs, intensity distribution when circular arc array is provided in radial at intervals of 0.3 mm to construct multi-tomographic image, is shown in FIGS. 21A-21C by perspective view, top plan view, and cross-sectional view on the pixel number 0, respectively.

Figure 22A:
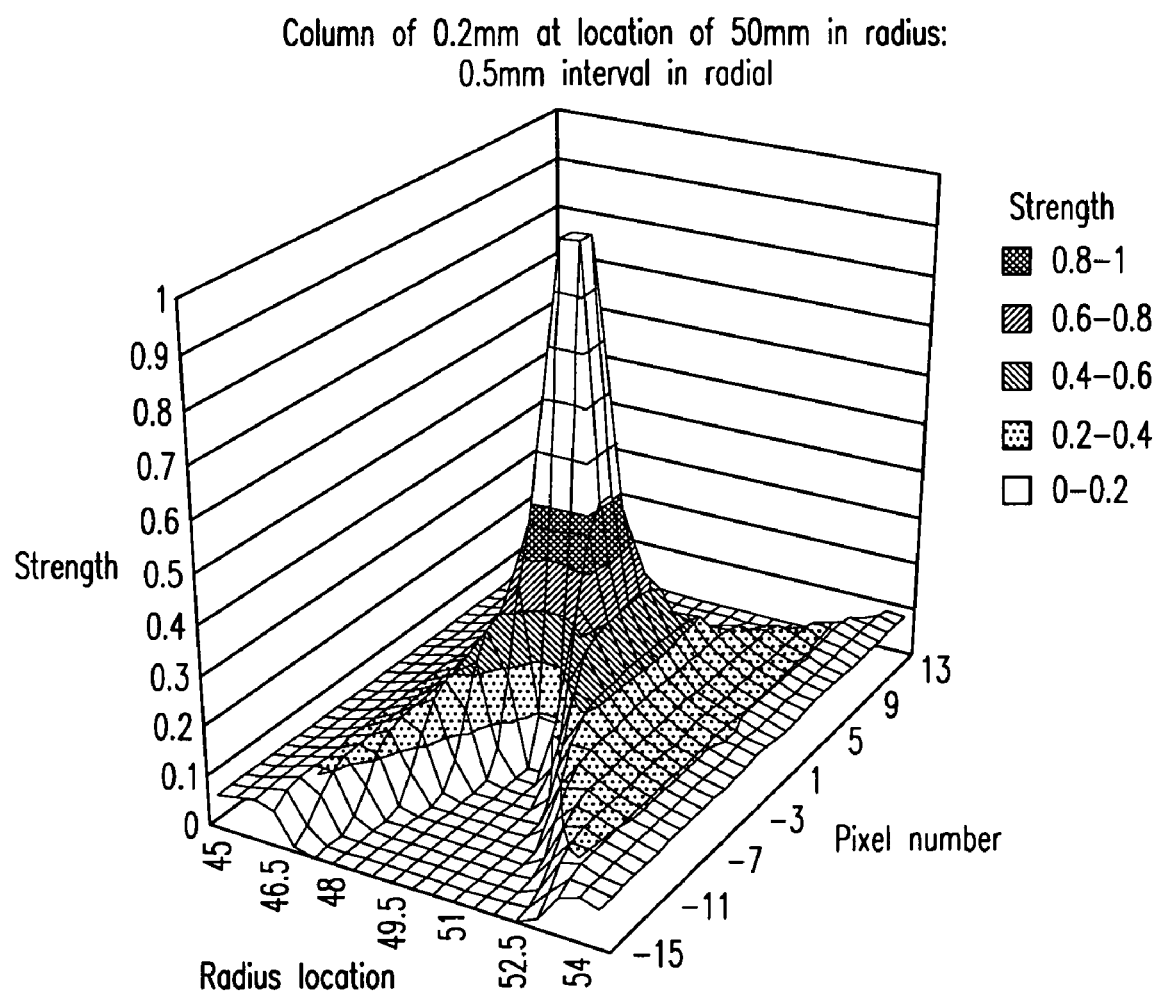
FIGS. 22A-22C show a perspective view, a top plan view, and a cross-sectional view wherein similarly, under the conditions that puts the column of 0.2 mm at location of 50 mm in radius and photographs, intensity distribution when circular arc array is provided in radial at intervals of 0.5 mm to construct multi-tomographic image, is shown on the pixel number 0, respectively.
Figure 22B:
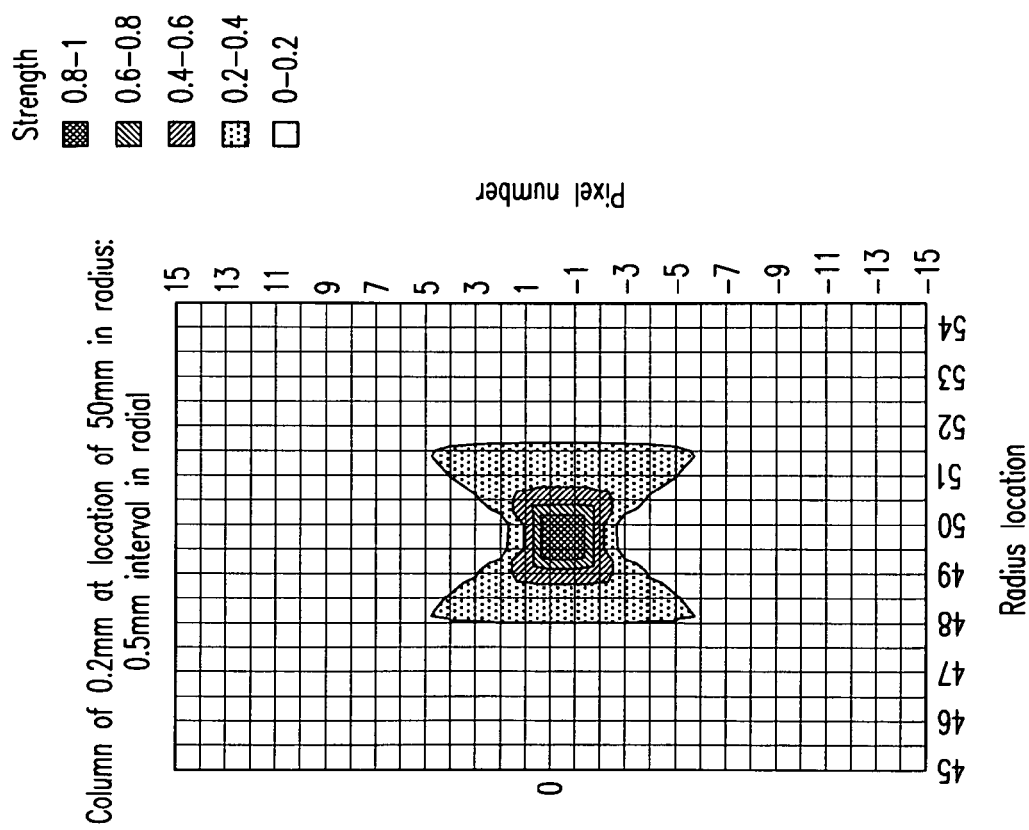
Figure 22C:
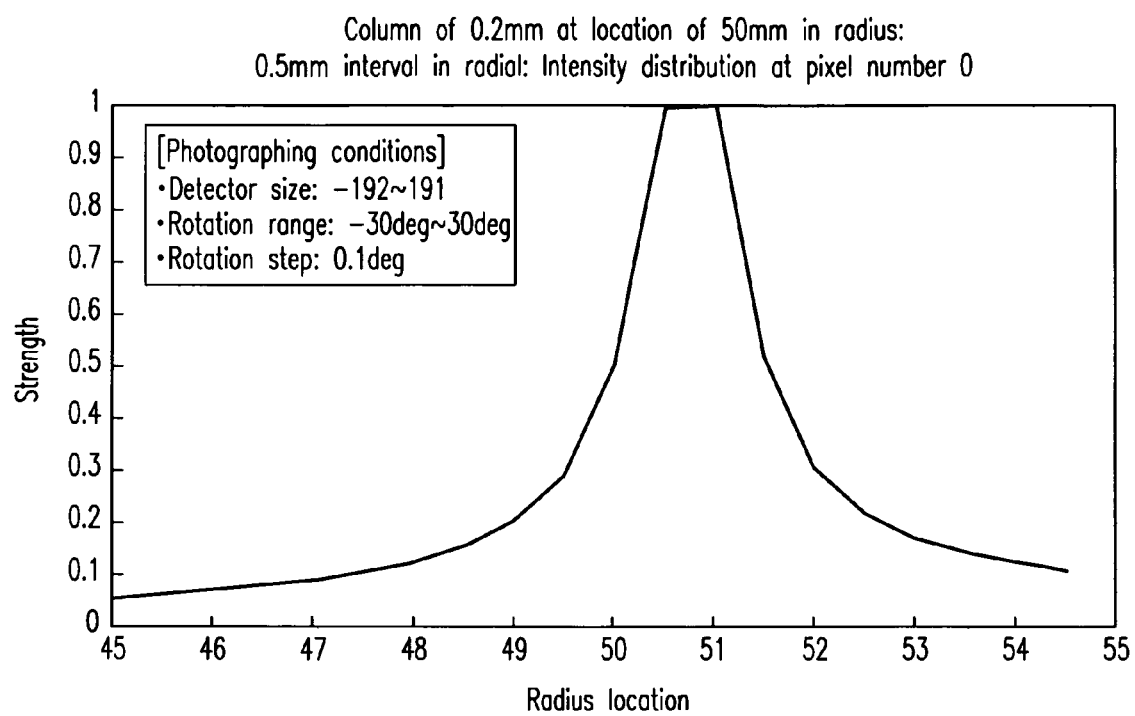

In the method of constructing multi-tomographic image of the present invention, as described above, under the conditions that puts the column of 0.2 mm at location of 50 mm in radius and photographs, intensity distribution when circular arc array is provided in radial at intervals of 0.5 mm to construct multi-tomographic image, is shown in FIGS. 22A-22C by perspective view, top plan view, and cross-sectional view on the pixel number 0, respectively.

Figure 23A:
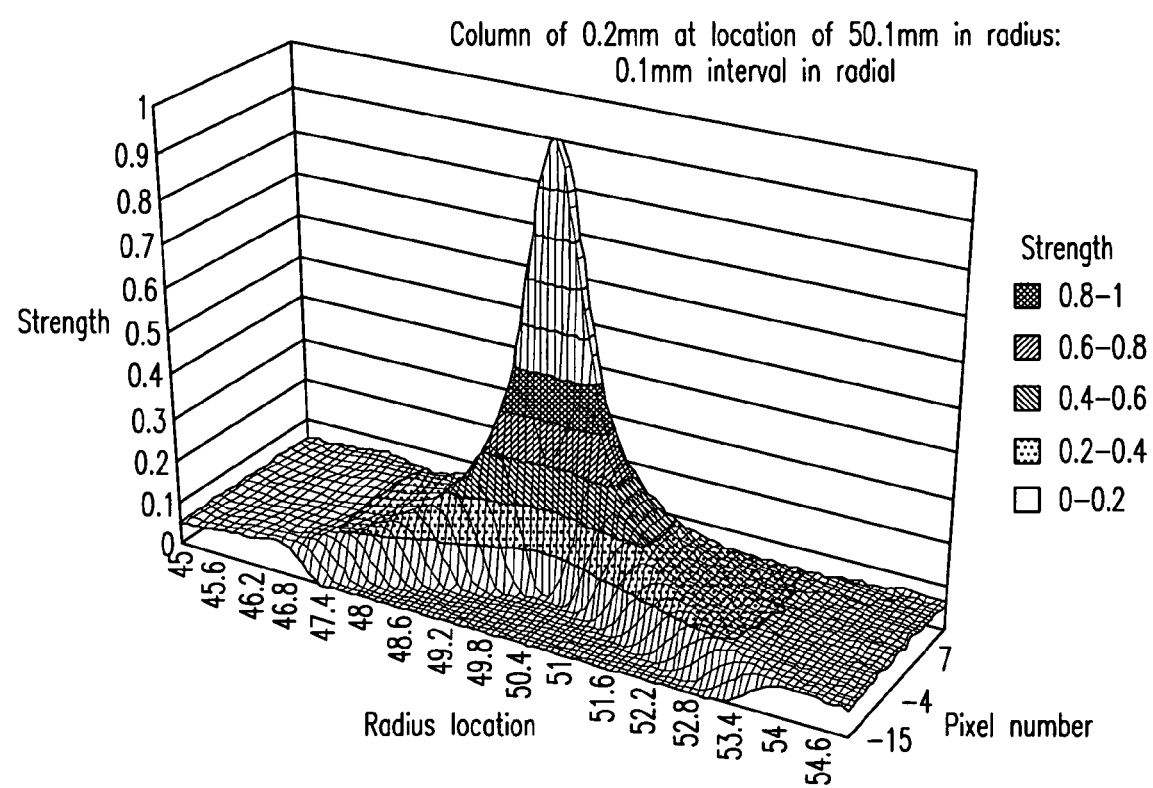
FIGS. 23A-23C show a perspective view, a top plan view, and a cross-sectional view wherein similarly, under the conditions that puts the column of 0.2mm at location of 50.1 mm in radius and photographs, intensity distribution when circular arc array is provided in radial at intervals of 0.1 mm to construct multi-tomographic image, is shown on the pixel number 0, respectively.
Figure 23B:
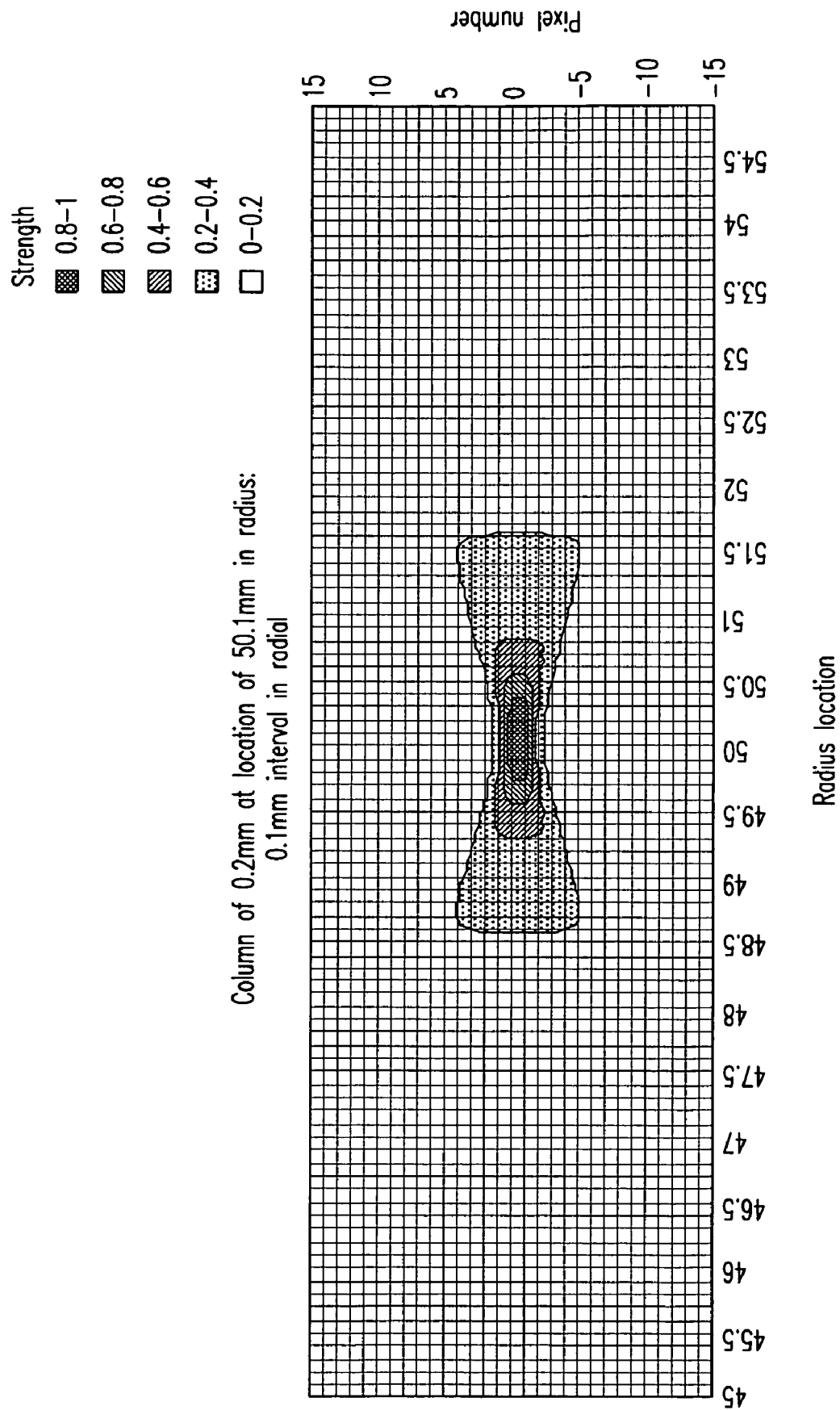
Figure 23C:
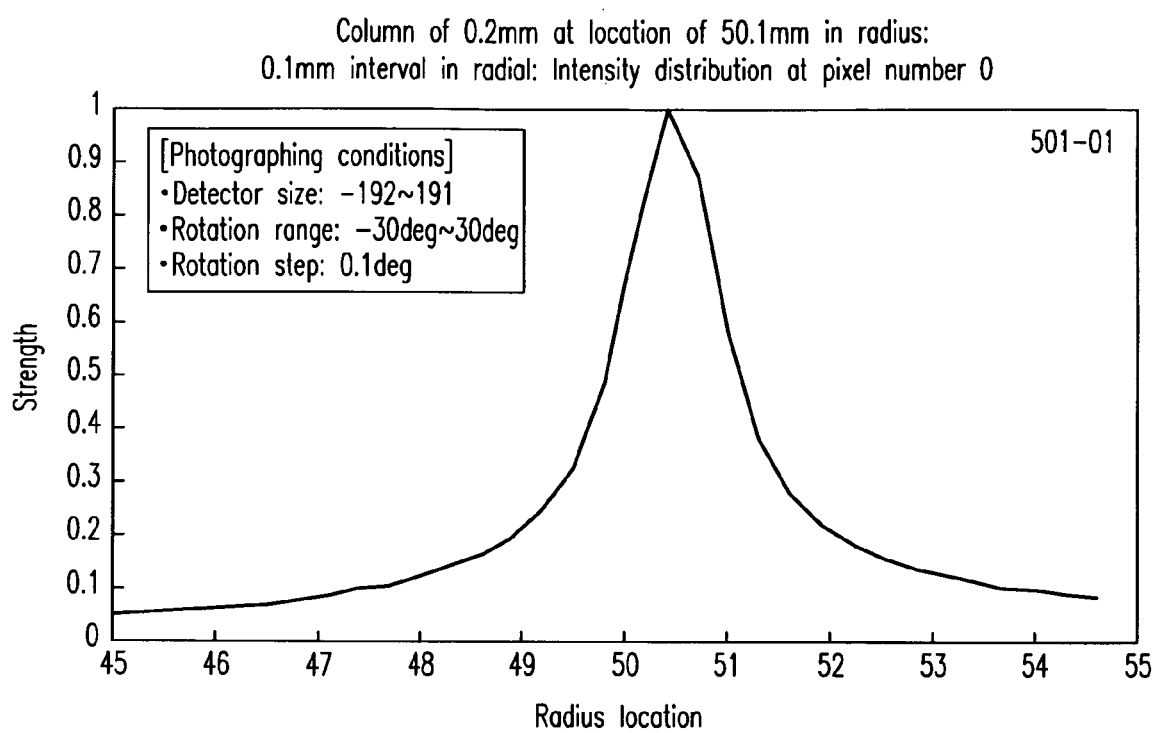

In the method of constructing multi-tomographic image of the present invention, as described above, under the conditions that puts the column of 0.2 mm at location of 50.1 mm in radius and photographs, intensity distribution when circular arc array is provided in radial at intervals of 0.1 mm to construct multi-tomographic image, is shown in FIGS. 23A-23C by perspective view, top plan view, and cross-sectional view on the pixel number 0, respectively.

Figure 24A:
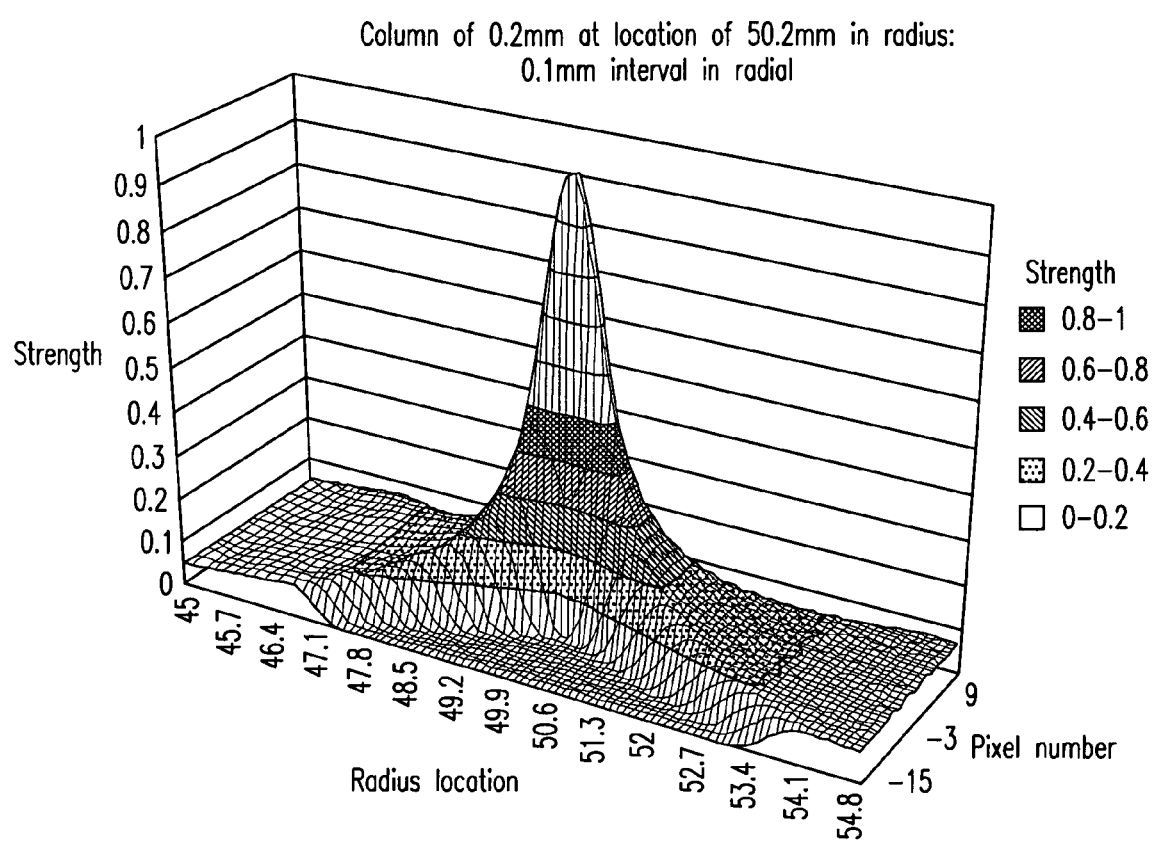
FIGS. 24A-24C show a perspective view, a top plan view, and a cross-sectional view wherein similarly, under the conditions that puts the column of 0.2 mm at location of 50.2 mm in radius and photographs, intensity distribution when circular arc array is provided in radial at intervals of 0.1 mm to construct multi-tomographic image, is shown on the pixel number 0, respectively.
Figure 24B:
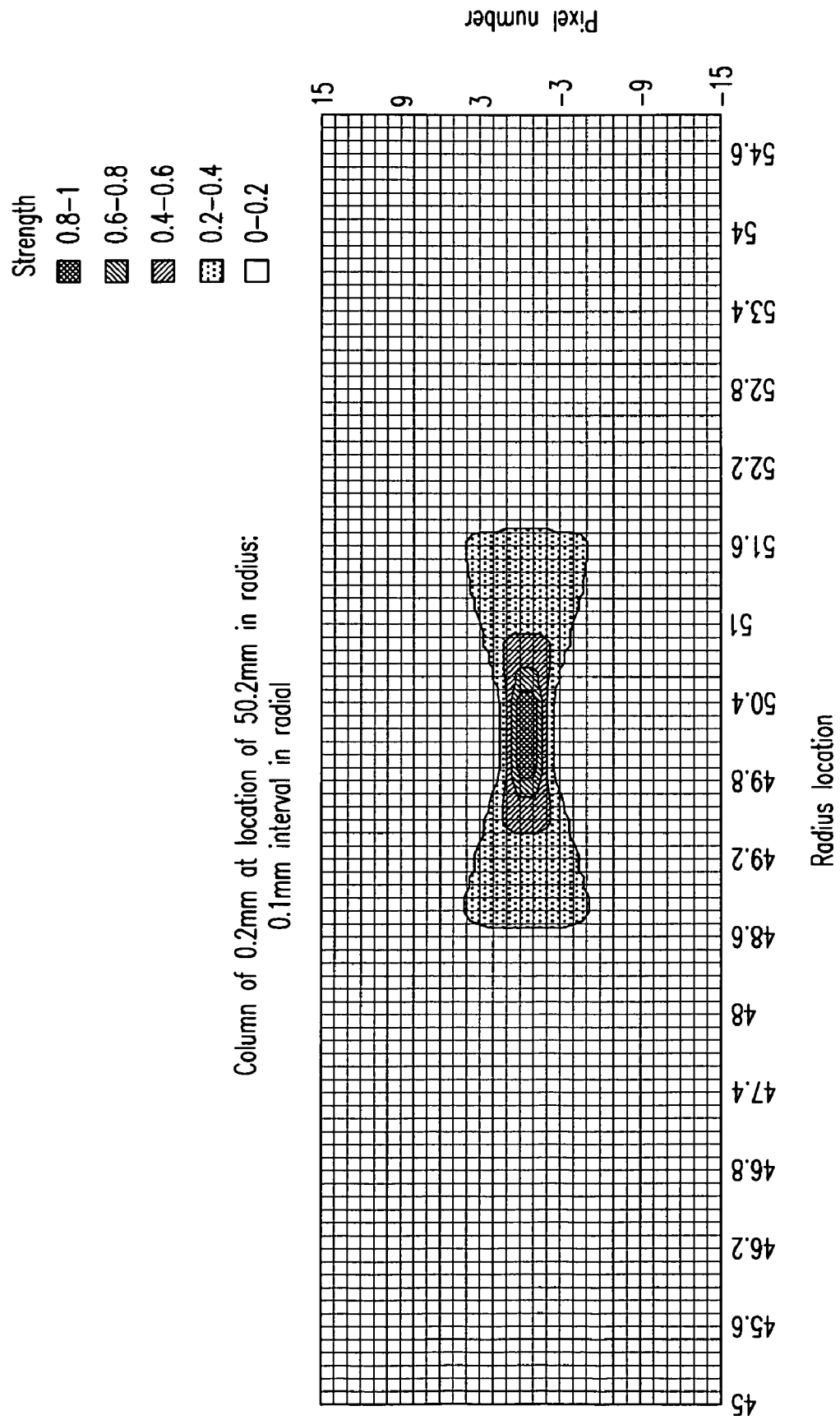
Figure 24C:
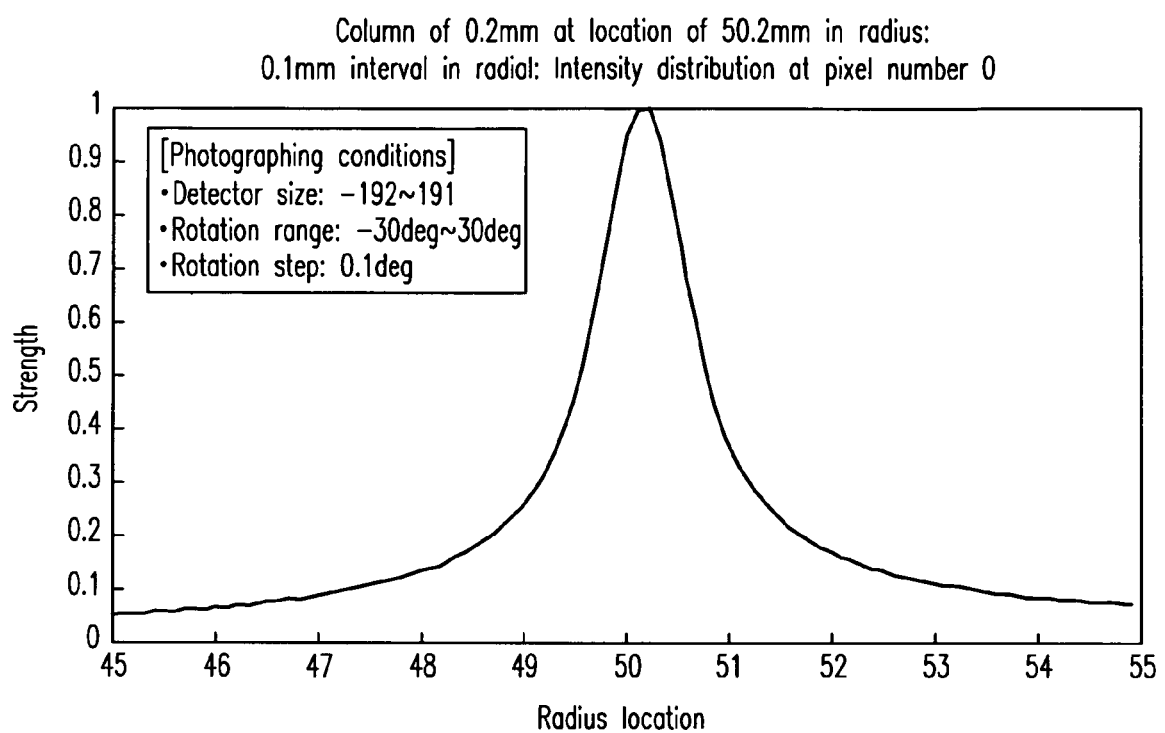

In the method of constructing multi-tomographic image of the present invention, as described above, under the conditions that puts the column of 0.2 mm at location of 50.2 mm in radius and photographs, intensity distribution when circular arc array is provided in radial at intervals of 0.1 mm to construct multi-tomographic image, is shown in FIGS. 24A-24C by perspective view, top plan view, and cross-sectional view on the pixel number 0, respectively.

Figure 25A:
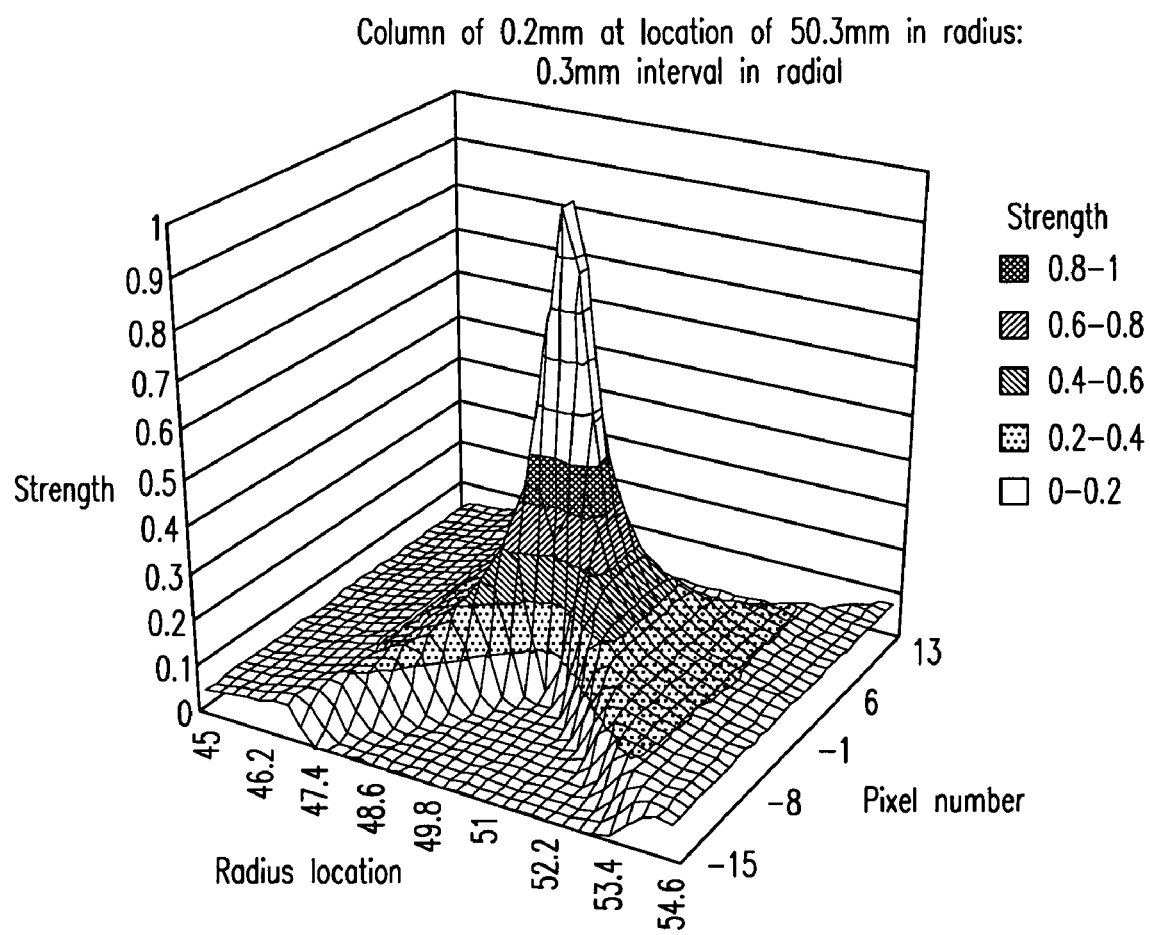
FIGS. 25A-25C show a perspective view, a top plan view, and a cross-sectional view wherein similarly, under the conditions that puts the column of 0.2 mm at location of 50.3 mm in radius and photographs, intensity distribution when circular arc array is provided in radial at intervals of 0.3 mm to construct multi-tomographic image, is shown on the pixel number 0, respectively.
Figure 25B:
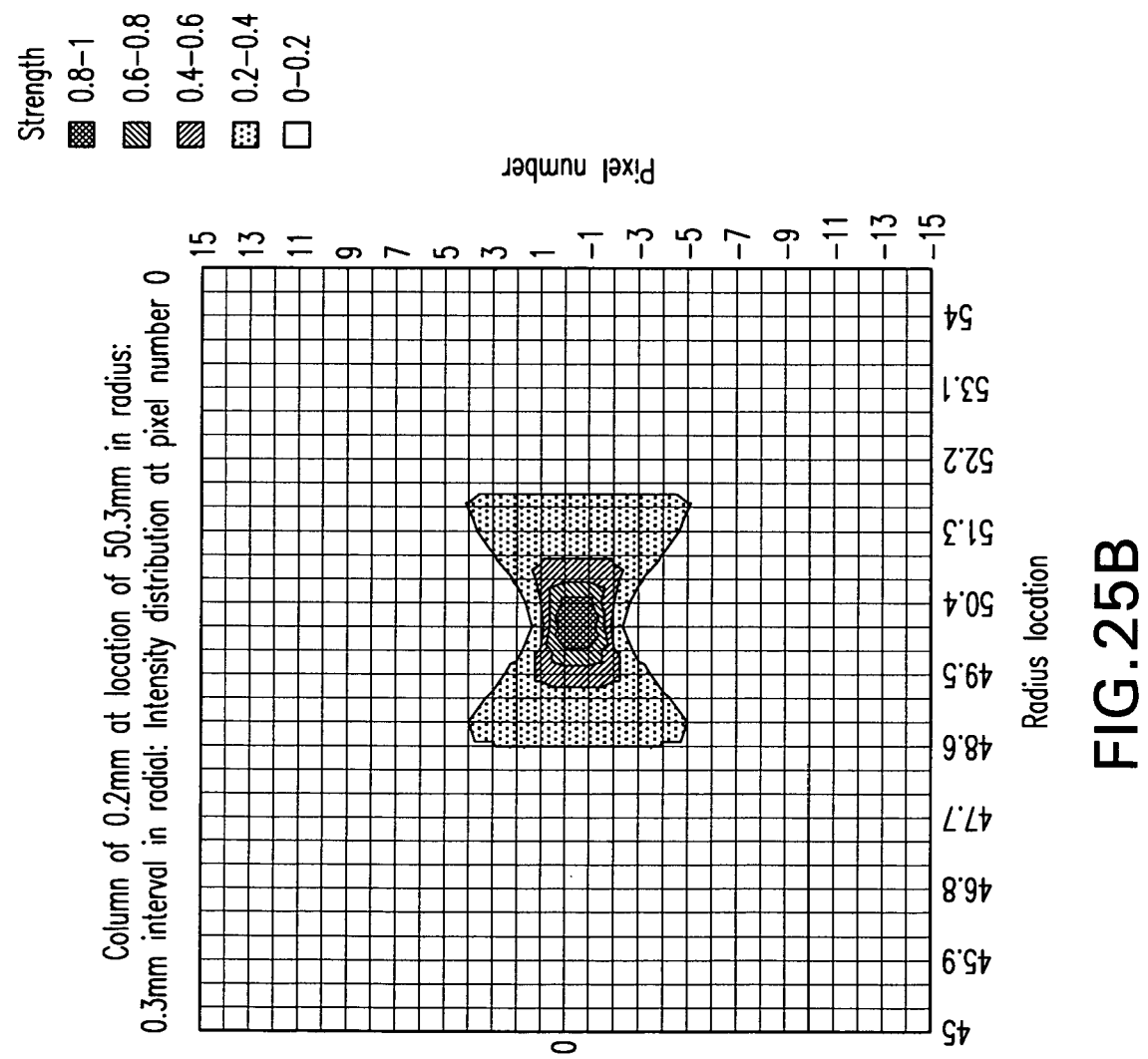
Figure 25C:
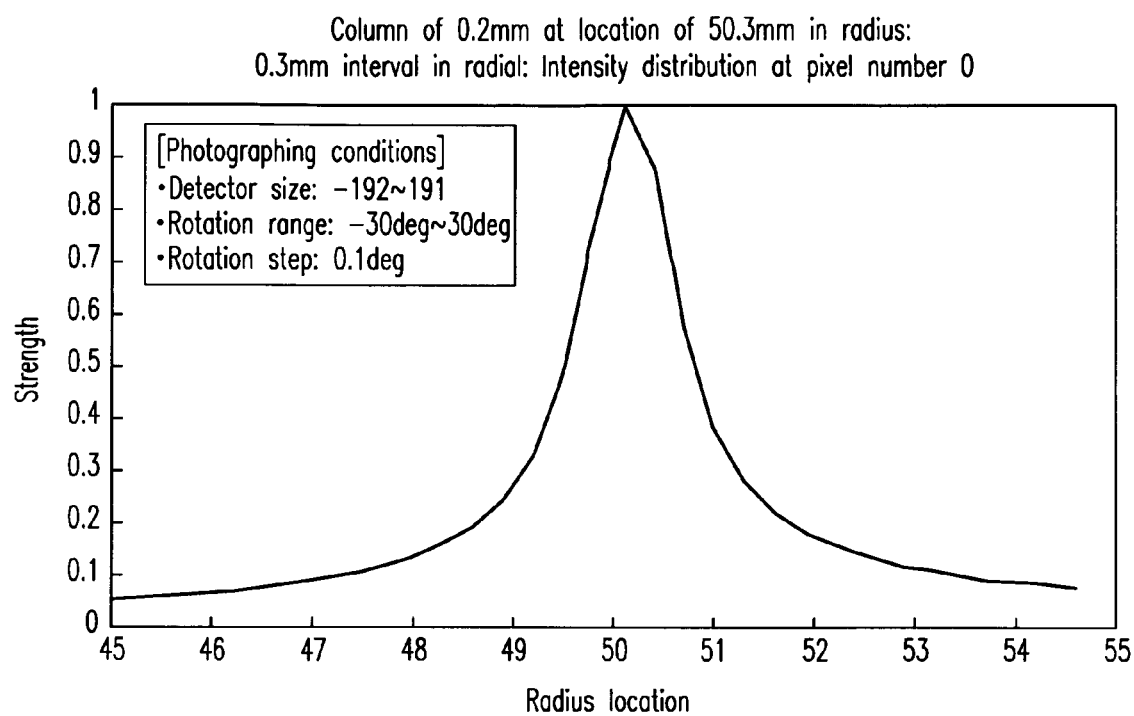

In the method of constructing multi-tomographic image of the present invention, as described above, under the conditions that puts the column of 0.2 mm at location of 50.3 mm in radius and photographs, intensity distribution when circular arc array is provided in radial at intervals of 0.3 mm to construct multi-tomographic image, is shown in FIGS. 25A-25C by perspective view, top plan view, and cross-sectional view on the pixel number 0, respectively.

Figure 26A:
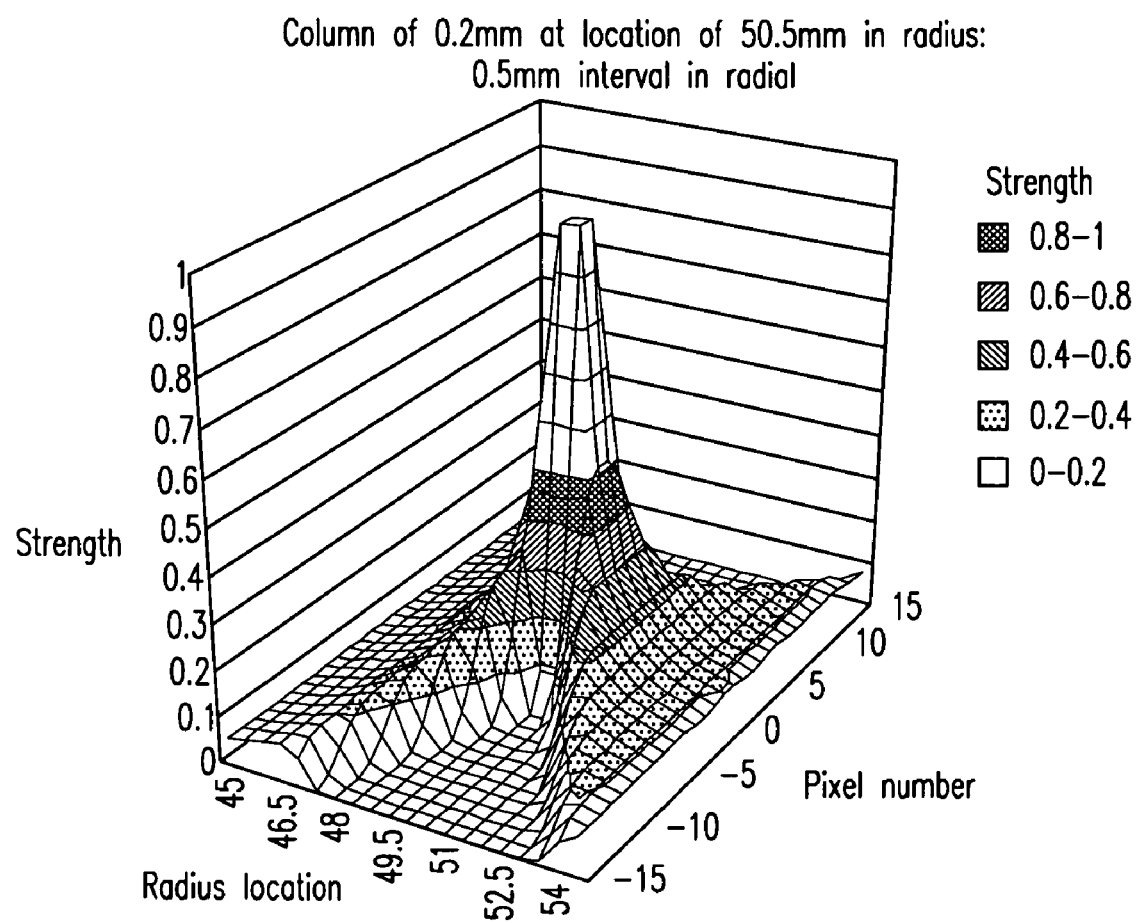
FIGS. 26A-26C a perspective view, a top plan view, and a cross-sectional view wherein similarly, under the conditions that puts the column of 0.2 mm at location of 50.5 mm in radius and photographs, intensity distribution when circular arc array is provided in radial at intervals of 0.5 mm to construct multi-tomographic image, is shown on the pixel number 0, respectively.
Figure 26B:
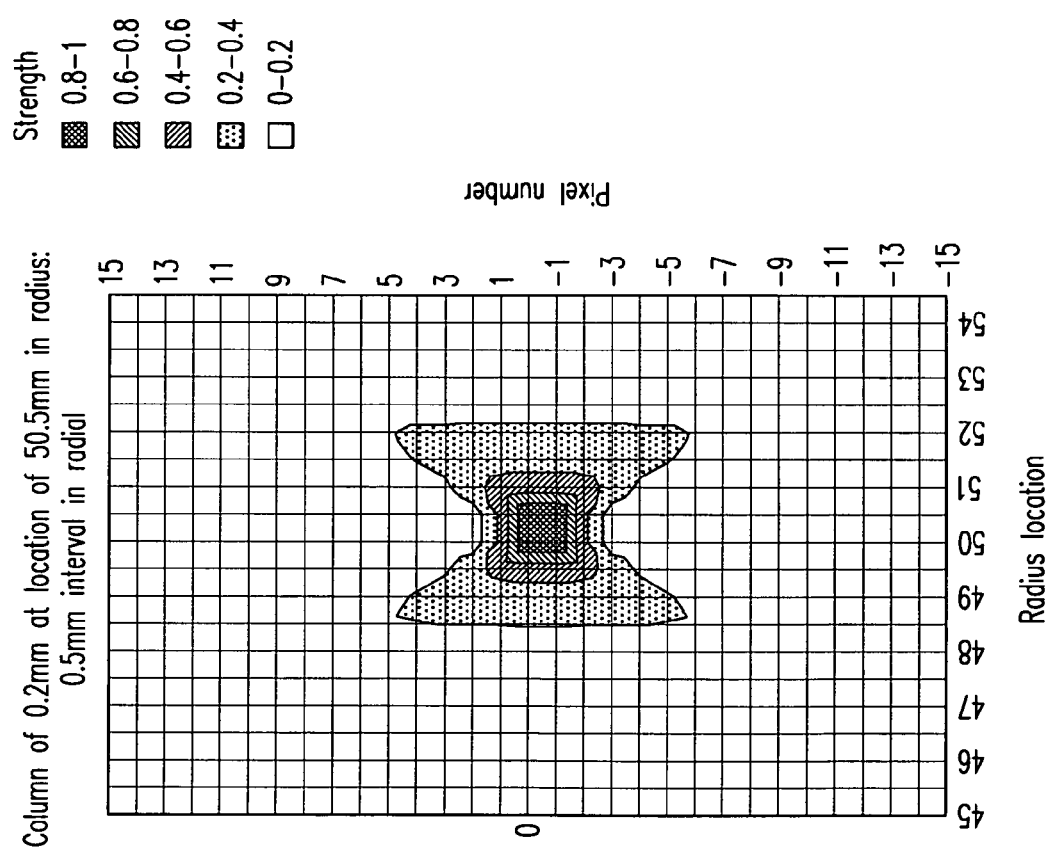
Figure 26C:
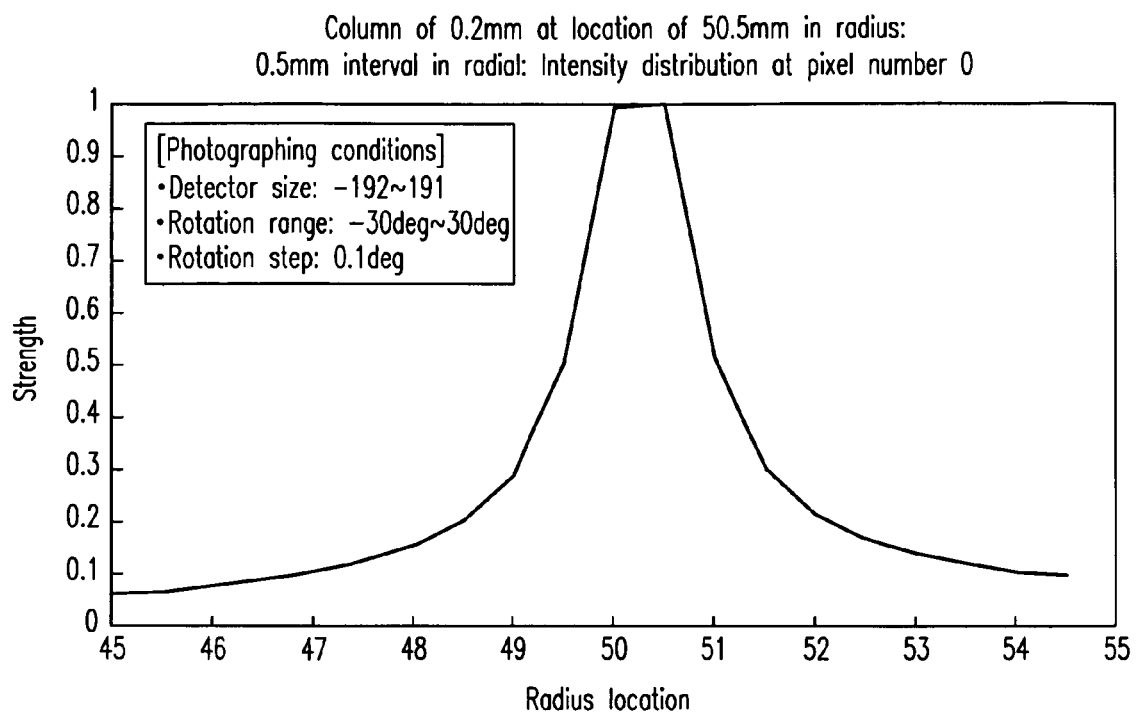

In the method of constructing multi-tomographic image of the present invention, as described above, under the conditions that puts the column of 0.2 mm at location of 50.5 mm in radius and photographs, intensity distribution when circular arc array is provided in radial at intervals of 0.5 mm to construct multi-tomographic image, is shown in FIGS. 26A-26C by perspective view, top plan view, and cross-sectional view on the pixel number 0, respectively.

Figure 27A:
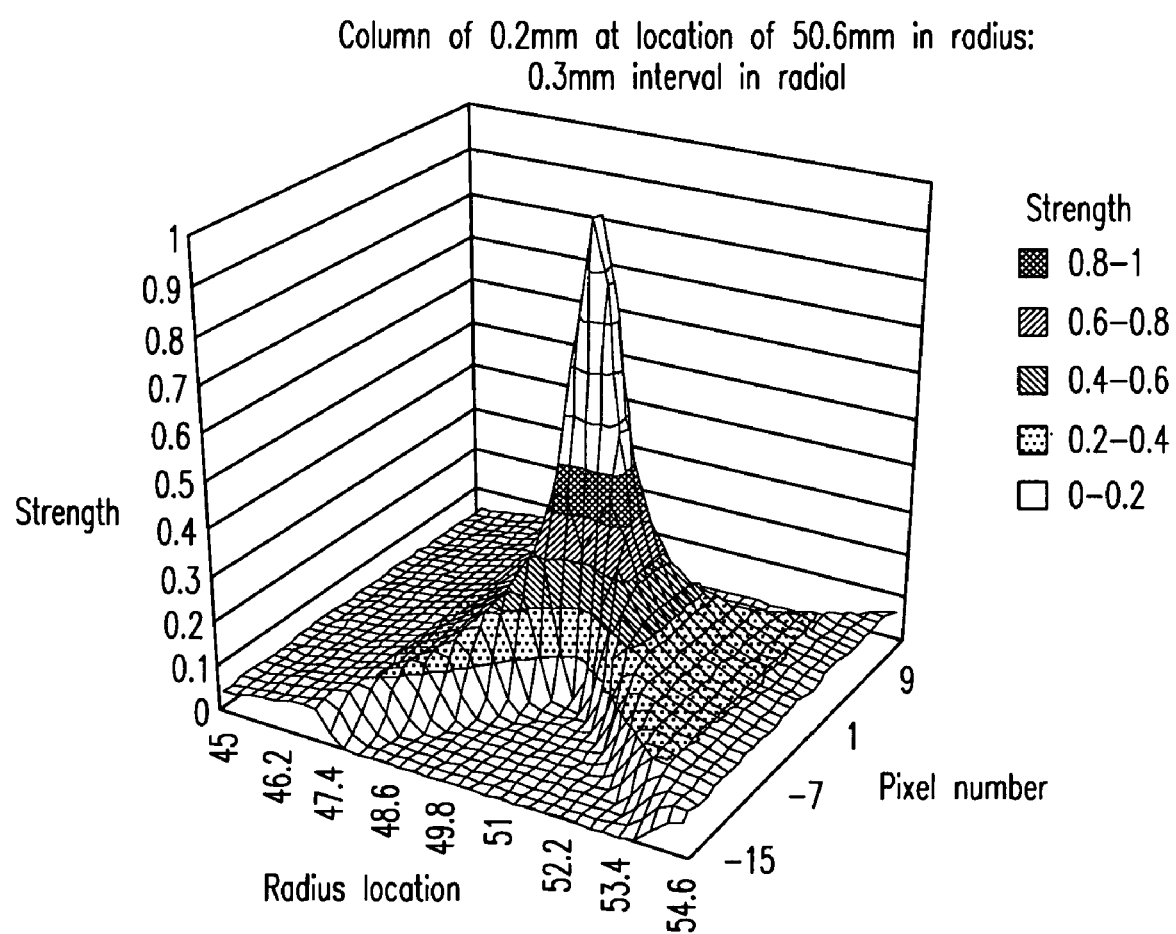
FIGS. 27A-27C show a perspective view, a top plan view, and a cross-sectional view wherein similarly, under the conditions that puts the column of 0.2 mm at location of 50.6 mm in radius and photographs, intensity distribution when circular arc array is provided in radial at intervals of 0.3 mm to construct multi-tomographic image, is shown on the pixel number 0, respectively.
Figure 27B:
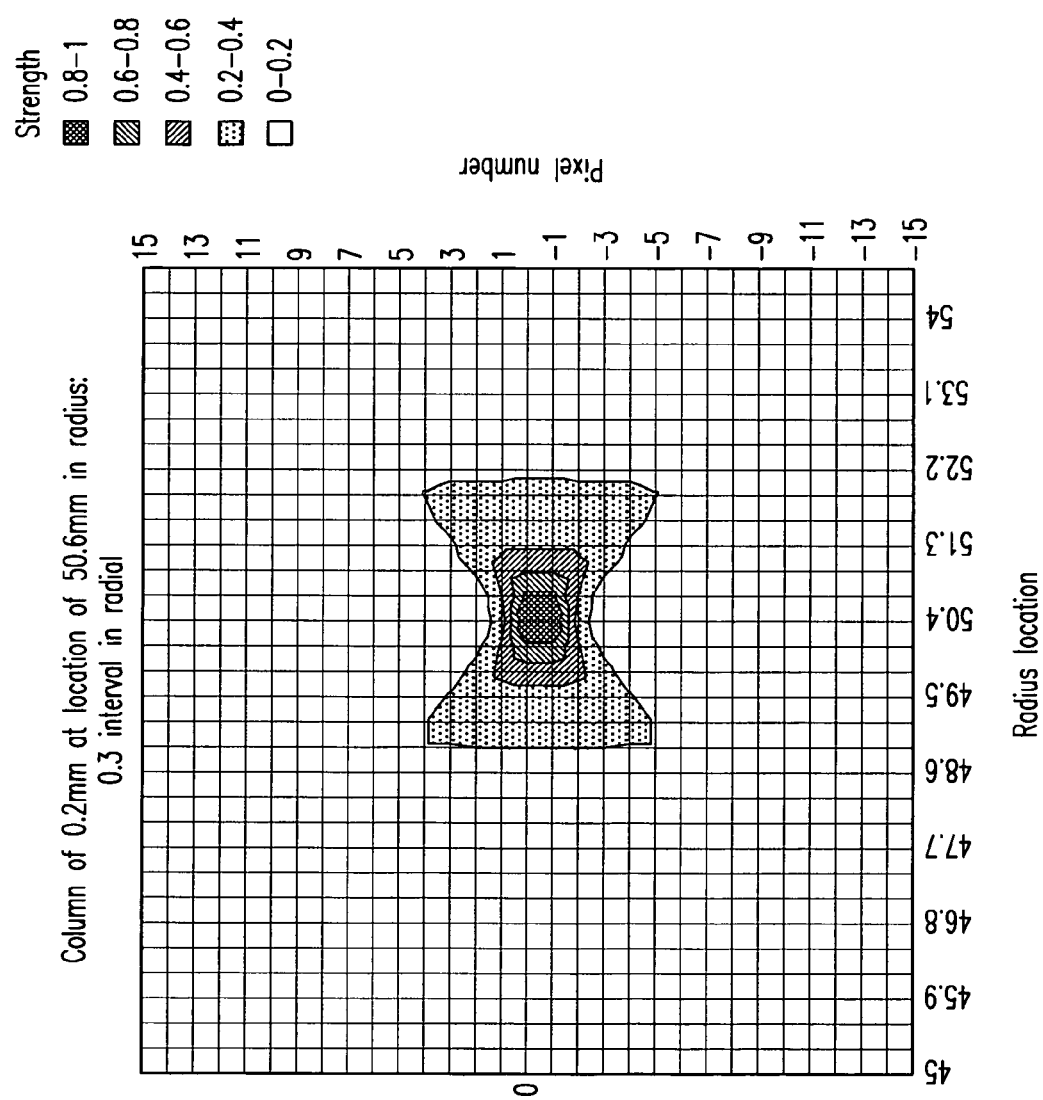
Figure 27C:
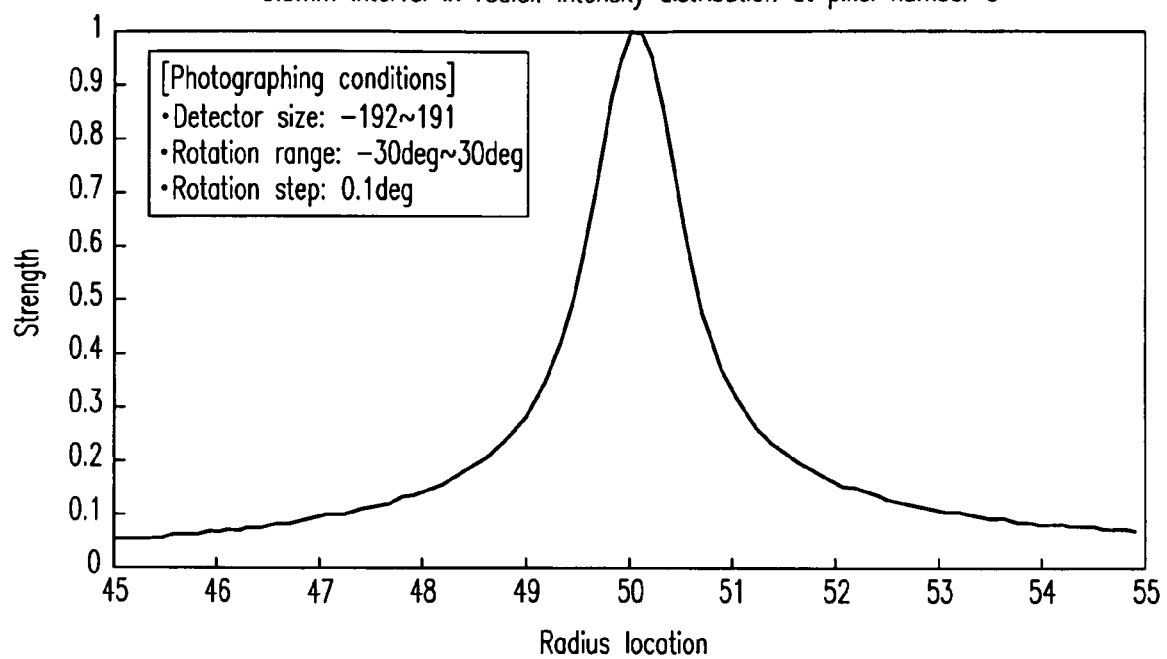

In the method of constructing multi-tomographic image of the present invention, as described above, under the conditions that puts the column of 0.2 mm at location of 50.6 mm in radius and photographs, intensity distribution when circular arc array is provided in radial at intervals of 0.3 mm to construct multi-tomographic image, is shown in FIGS. 27A-27C by perspective view, top plan view, and cross-sectional view on the pixel number 0, respectively.

Figure 28A:
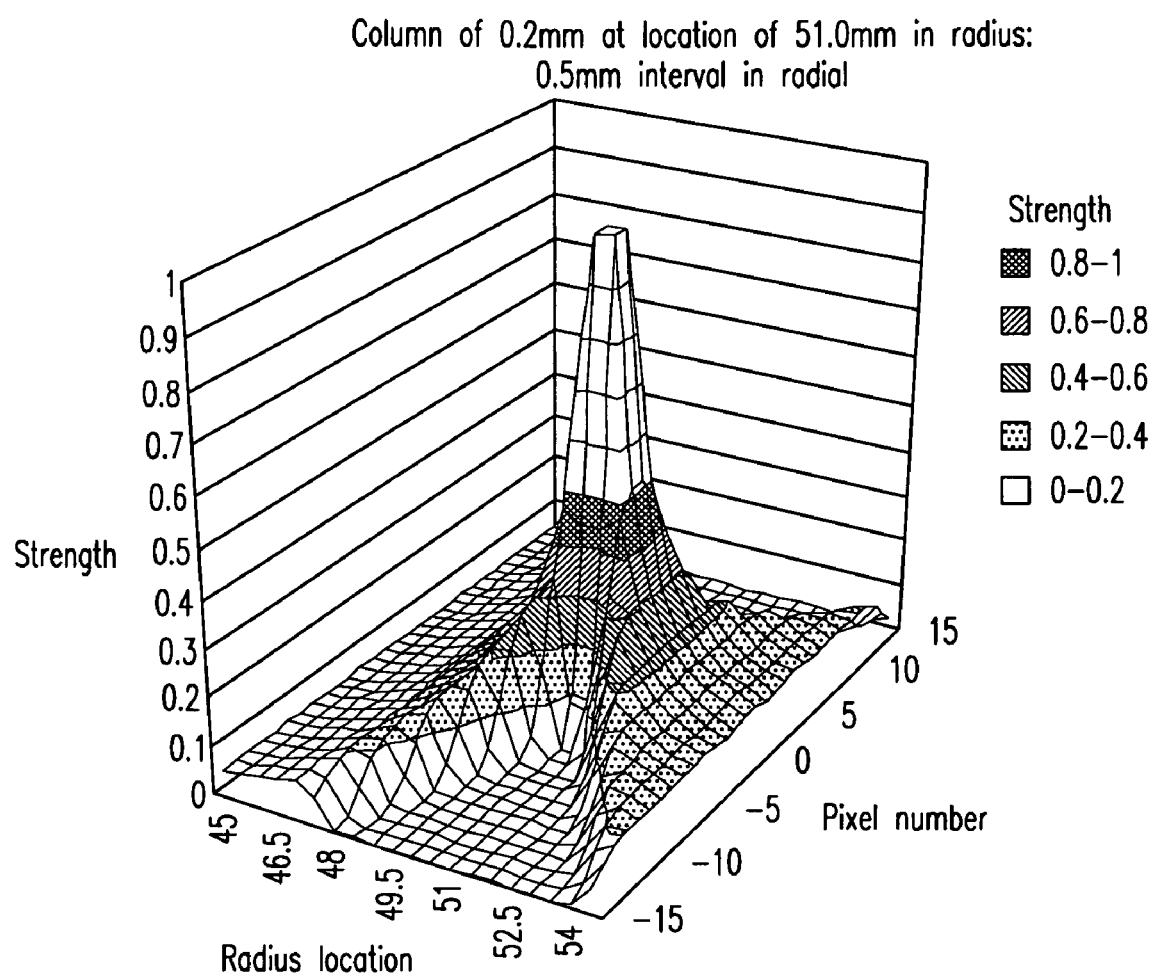
FIGS. 28A-28C show a perspective view, a top plan view, and a cross-sectional view wherein similarly, under the conditions that puts the column of 0.2 mm at location of 51.0 mm in radius and photographs, intensity distribution when circular arc array is provided in radial at intervals of 0.5 mm to construct multi-tomographic image, is shown on the pixel number 0, respectively.
Figure 28B:
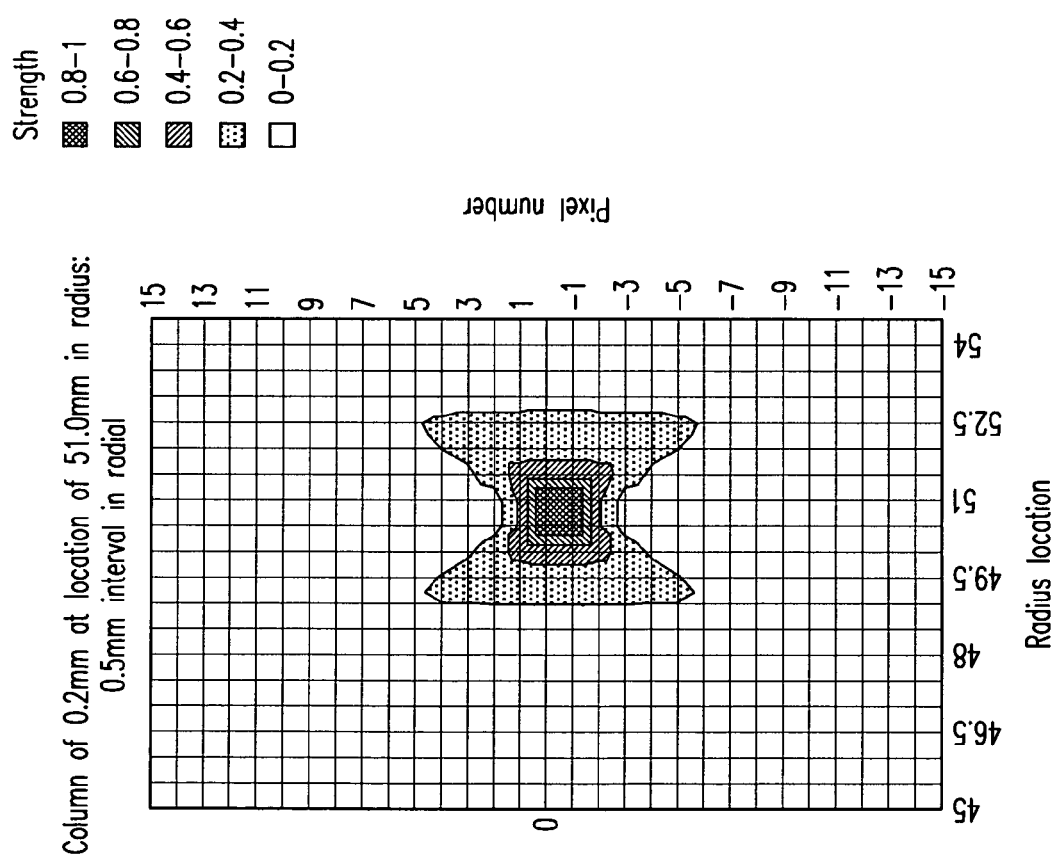
Figure 28C:
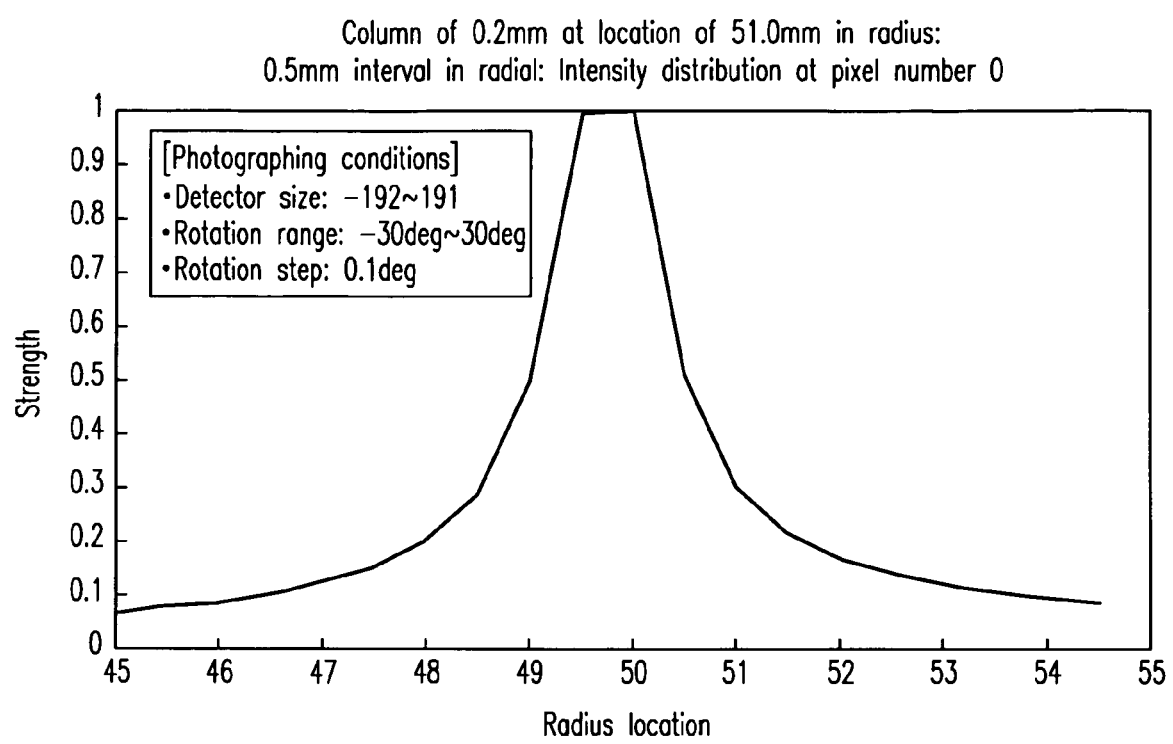

In the method of constructing multi-tomographic image of the present invention, as described above, under the conditions that puts the column of 0.2 mm at location of 51.0 mm in radius and photographs, intensity distribution when circular arc array is provided in radial at intervals of 0.5 mm to construct multi-tomographic image, is shown in FIGS. 28A-28C by perspective view, top plan view, and cross-sectional view on the pixel number 0, respectively.

In this way, in the above-described multi-tomographic image constructing method and the digital 3 D X-ray photographing apparatus, though only the image at intervals of 0.5 mm could be obtained, but according to the present invention, even at 0.3 mm interval and at 0.1 mm interval, the image of further arbitrary location (for example, 0.1 mm interval et al.) from the location of the prior application can be constructed.

According to the present invention, the stereoscopic image of whole diagnosis region can be obtained easily, by slicing multi-tomographic image obtained as described above transversally and by using the volume rendering software.

Moreover, in this embodiment, as a x-ray imaging means, CCD sensor is explained as an example, but, the present invention is not limited to this, and for example, a TFT sensor, a MOS sensor, an XII (X-ray Image Intensifier) sensor, a FPD (Flat Panel Detector) sensor, and a CdTe sensor et al can also be used as an x-ray imaging means, to perform the multi-tomographic image X-ray photographing similar to described above.

The present invention is not limited to the above dental radiography apparatus, and can be applied to the medical X-ray examination apparatus, resulting in an attainment of large effect.

In addition, the present invention can be applied also to a nondestructive inspection system, and the effect thereof is immeasurable.

What is claimed is:

1. A method of constructing multiple tomographic images of a subject, comprising:
   irradiating X-rays onto a subject by operation of an X-ray source;
   detecting the X-rays that pass through the subject by an X-ray imaging CCD device;
   providing an imaging system by oppositely arranging and fixing the X-ray imaging device and the X-ray source at a certain distance, centered on the subject;
   revolving said imaging system about an axis centered on the subject;
   storing image information being obtained by the X-ray imaging device with a single X-ray radiography operation into a large-capacity frame image storage device as a frame image;
   digital-processing respective frame images extracted from the large-capacity frame image storage device to form panoramic images;
   storing the panoramic images in a large-capacity processed image storage device;
   displaying the panoramic images stored in the large-capacity processed image storage device;
   arraying a certain frame image taken out of the panoramic images stored in the large-capacity processed image storage device onto a circular arc arrangement, by linear-interpolating the pixel value with the area ratio per circular arc shaped square cell elements across plural pixels;
   performing a polar coordinate transformation sequentially with respect to each frame image by using the angle rotated while obtaining said each frame image as a unit angle; and
   adding the frame images sequentially by shifting every unit angle to construct a tomographic image on the radius positioned at the desired location.

2. A method according to claim 1, wherein the polar coordinate transformed images are made from the tomographic image of each radius obtained by the method of constructing multiple tomographic images, and the 3D image is generated from the the polar coordinate transformed images by using a volume rendering software.

3. A method according to claim 1, wherein:
   the X-ray imaging device includes an X-ray sensor; and
   the X-ray sensor is selected from the group consisting of a CCD, a TFT sensor, a MOS sensor, an XII (X-ray Image Intensifier) sensor, an FPD (Flat Panel Detector) sensor, and a CdTe sensor.

4. A digital 3D X-ray radiography apparatus, comprising:
   an X-ray source for irradiating X-rays onto a subject;
   an X-ray imaging device for detecting X-rays passing through a subject;
   a revolving device for rotating an imaging system including oppositely arranging and fixing the X-ray imaging device and the X-ray source at a certain distance, centered on the subject;
   a large-capacity frame image storage device for storing therein image information being obtained by the X-ray imaging device as a frame image;
   an image processing device for extracting the frame image from the large-capacity frame image storage device, and for forming a panoramic image with digital processing;
   a large-capacity processed image storage device for storing the panoramic image;
   a tomographic images display and storing device for displaying and storing each panoramic image in the large-capacity processed image storage device, and an output device for outputting film of the panoramic image;
   a storage device for storing frame images of plural pieces which have all subject information on radius of revolution, in the large-capacity frame image storage device, by X-ray radiographing with the imaging system in a X-ray radiography operation;
   an arranging device for arranging a certain frame image taken out of the processed panoramic images stored in the large-capacity processed image storage device onto a circular arc arrangement, by linear-interpolating the pixel value with the area ratio per the circular arc shaped square cell elements across plural pixels; and
   an adding device for adding sequentially the above processed respective frame images, by performing such a process sequentially with respect to each frame image, by using the angle rotated while obtaining each frame image as a unit angle, and by shifting every unit angle, to construct a tomographic image at the radius positioned at a desired location.

5. A digital 3D X-ray photographing apparatus according to claim 4, wherein:
   the polar coordinate transformed images are made from the tomographic image of each radius obtained by the 3D X-ray radiography apparatus; and
   a 3D image is generated by using a volume rendering software, thereby obtaining a stereoscopic image of all diagnosis regions.

6. A digital 3D X-ray radiography apparatus according to claim 4, wherein:
   the X-ray imaging means includes an X-ray sensor and the X-ray sensor is selected from the group consisting of a CCD, a TFT sensor, a MOS sensor, an XII(X-ray Image Intensifier) sensor, an FPD (Flat Panel Detector) sensor, and a CdTe sensor.

* * * * *